United States Patent
Yamada et al.

(10) Patent No.: US 10,231,807 B2
(45) Date of Patent: Mar. 19, 2019

(54) ZIRCONIA SINTERED BODY, ZIRCONIA COMPOSITION, ZIRCONIA PRE-SINTERED BODY AND PREPARING METHOD THEREOF, AND DENTAL PROSTHESIS

(71) Applicant: KURARAY NORITAKE DENTAL INC., Kurashiki-shi (JP)

(72) Inventors: Yoshihisa Yamada, Miyoshi (JP); Atsushi Matsumoto, Miyoshi (JP); Yoshihisa Ito, Miyoshi (JP)

(73) Assignee: KURARAY NORITAKE DENTAL INC., Kurashiki-shi (JP)

( * ) Notice: Subject to any disclaimer, the term of this patent is extended or adjusted under 35 U.S.C. 154(b) by 208 days.

(21) Appl. No.: 14/890,239

(22) PCT Filed: May 8, 2014

(86) PCT No.: PCT/JP2014/062365
§ 371 (c)(1),
(2) Date: Nov. 10, 2015

(87) PCT Pub. No.: WO2014/181828
PCT Pub. Date: Nov. 13, 2014

(65) Prior Publication Data
US 2016/0074142 A1    Mar. 17, 2016

(30) Foreign Application Priority Data

May 10, 2013    (JP) .................................. 2013-100619

(51) Int. Cl.
*B28B 5/00*    (2006.01)
*B32B 3/26*    (2006.01)
(Continued)

(52) U.S. Cl.
CPC .............. *A61C 13/083* (2013.01); *B28B 5/00* (2013.01); *B32B 3/26* (2013.01); *B32B 5/16* (2013.01);
(Continued)

(58) Field of Classification Search
CPC ......... A61C 13/083; B32B 18/00; B32B 3/26; B32B 5/30; B32B 5/16; B32B 5/00;
(Continued)

(56) References Cited

U.S. PATENT DOCUMENTS 7,981,531 B2    7/2011    Rheinberger et al.
8,034,264 B2    10/2011    Ritzberger et al.
(Continued)

FOREIGN PATENT DOCUMENTS

CN    101351183 A    1/2009
CN    102098981 A    6/2011
(Continued)

OTHER PUBLICATIONS

Korean Office Action dated Dec. 13, 2016 in Patent Application No. 10-2015-7034754 (without English Translation).
(Continued)

*Primary Examiner* — Shane Fang
(74) *Attorney, Agent, or Firm* — Oblon, McClelland, Maier & Neustadt, L.L.P.

(57) ABSTRACT

A method for preparing a zirconia composition comprises preparing a plurality of powders for lamination; the lamination powders containing zirconia, a stabilizer(s) suppressing phase transition of zirconia and a pigment(s) at respective different pigment content ratios, and laminating the lamination powders in a mold. In the laminating step, the mold is vibrated after at least two lamination powders are charged into the mold.

15 Claims, 7 Drawing Sheets

(51) Int. Cl.
- *B32B 5/16* (2006.01)
- *B32B 5/30* (2006.01)
- *A61C 13/09* (2006.01)
- *B32B 18/00* (2006.01)
- *C04B 35/48* (2006.01)
- *A61C 13/083* (2006.01)
- *C04B 35/486* (2006.01)
- *C04B 35/626* (2006.01)
- *C04B 35/645* (2006.01)

(52) U.S. Cl.
CPC ............... *B32B 5/30* (2013.01); *B32B 18/00* (2013.01); *C04B 35/48* (2013.01); *C04B 35/486* (2013.01); *C04B 35/62645* (2013.01); *C04B 35/62675* (2013.01); *C04B 35/6455* (2013.01); *A61C 13/09* (2013.01); *B32B 2264/102* (2013.01); *B32B 2264/107* (2013.01); *B32B 2535/00* (2013.01); *C04B 2235/3206* (2013.01); *C04B 2235/3208* (2013.01); *C04B 2235/3217* (2013.01); *C04B 2235/3224* (2013.01); *C04B 2235/3225* (2013.01); *C04B 2235/3229* (2013.01); *C04B 2235/3232* (2013.01); *C04B 2235/3241* (2013.01); *C04B 2235/3272* (2013.01); *C04B 2235/3418* (2013.01); *C04B 2235/604* (2013.01); *C04B 2235/6026* (2013.01); *C04B 2235/765* (2013.01); *C04B 2235/81* (2013.01); *C04B 2235/96* (2013.01); *C04B 2235/9653* (2013.01); *C04B 2235/9661* (2013.01); *C04B 2237/348* (2013.01); *C04B 2237/58* (2013.01)

(58) Field of Classification Search
CPC ........ B32B 2264/102; B32B 2264/107; C04B 2235/3272; C04B 2235/3224; C04B 2235/3217; C04B 2235/3225
See application file for complete search history.

(56) References Cited

U.S. PATENT DOCUMENTS

| | | |
|---|---|---|
| 8,541,329 B2 | 9/2013 | Ritzberger et al. |
| 8,691,122 B2 | 4/2014 | Rheinberger et al. |
| 8,721,336 B2 | 5/2014 | Rheinberger et al. |
| 8,877,664 B2 | 11/2014 | Ito et al. |
| 2007/0292597 A1 | 12/2007 | Ritzberger et al. |
| 2008/0064011 A1 | 3/2008 | Rheinberger et al. |
| 2008/0306168 A1 | 12/2008 | Craig et al. |
| 2011/0183297 A1 | 7/2011 | Thiel et al. |
| 2011/0236855 A1 | 9/2011 | Rheinberger et al. |
| 2011/0236857 A1 | 9/2011 | Rheinberger et al. |
| 2011/0319254 A1 | 12/2011 | Ritzberger et al. |
| 2012/0214661 A1 | 8/2012 | Ito et al. |
| 2012/0308837 A1 | 12/2012 | Schlechtriemen et al. |
| 2014/0070435 A1 | 3/2014 | Thiel et al. |
| 2015/0050619 A1 | 2/2015 | Thiel et al. |
| 2015/0246459 A1 | 9/2015 | Dorn et al. |

FOREIGN PATENT DOCUMENTS

| | | | |
|---|---|---|---|
| CN | 102153284 A | 8/2011 | |
| CN | 102285795 A | 12/2011 | |
| DE | 10 2006 024 489 A1 | 11/2007 | |
| EP | 1 859 757 A2 | 11/2007 | |
| EP | 2468699 A1 | 6/2012 | |
| EP | 2529694 A1 | 12/2012 | |
| JP | 06-024940 A | 2/1994 | |
| JP | 08-138555 A | 5/1996 | |
| JP | 2004 35332 | 2/2004 | |
| JP | 2004-181520 A | 7/2004 | |
| JP | 2004-284840 A | 10/2004 | |
| JP | 2005-112662 A | 4/2005 | |
| JP | 2008 68079 | 3/2008 | |
| JP | 2010-105174 * | 5/2010 | ............ B28B 13/00 |
| JP | 2011-178610 A | 9/2011 | |
| JP | 2012-41239 A | 3/2012 | |
| JP | 2012 250022 | 12/2012 | |
| KR | 10-2012-0062705 A | 6/2012 | |
| WO | WO 2011/021698 A1 | 2/2011 | |
| WO | WO 2013/156483 A1 | 10/2013 | |

OTHER PUBLICATIONS

Combined Office Action and Search Report issued Oct. 27, 2016 in Chinese Application No. 201480026447.4 (with English translation of Categories of Cited Documents).

International Search Report dated Jul. 29, 2014 in PCT/JP14/062365 Filed May 8, 2014.

Combined Office Action and Search Report dated May 26, 2017 in Chinese Patent Application No. 201480026447.4 (with English translation of category of cited documents).

Office Action dated Dec. 12, 2017 in Japanese Patent Application No. 2015-515891.

Japanese Office Action dated May 15, 2018, in Japanese Patent Application No. 2015-515891 (with its English Translation).

Chinese Office Action (Decision of Rejection) dated Jul. 27, 2018, in Chinese Patent Application No. 201480026447.4.

Chen, "Civil engineering material test training", Jun. 30, 2009, published by China Building Materials Press, pp. 104 and copyright page.

Extended European Search Report dated Dec. 6, 2016 in Patent Application No. 14795059.6.

\* cited by examiner

ZIRCONIA SINTERED BODY, ZIRCONIA COMPOSITION, ZIRCONIA PRE-SINTERED BODY AND PREPARING METHOD THEREOF, AND DENTAL PROSTHESIS

CROSS-REFERENCE TO RELATED APPLICATION

The present application is based upon and claims the benefit of the priority of Japanese patent application No. 2013-100619 filed on May 10, 2013, the disclosure of which is incorporated herein in its entirety by reference thereto.

TECHNICAL FIELD

The present invention relates to a zirconia sintered body. The present invention also relates to a composition and pre-sintered body (calcined body) for manufacturing the zirconia sintered body. The present invention also relates to methods of preparing the zirconia sintered body, composition and pre-sintered body. The present invention further relates to a dental prosthesis (prosthetic material) having the zirconia sintered body.

BACKGROUND

Ceramics made of sintered body of zirconium oxide (IV) ($ZrO_2$) (referred to as "zirconia" hereinafter) has been used in various fields. The zirconia sintered body having high strength has been applied for a dental prosthetic material, tool, etc., for example. In design of such a zirconia product, change in colors is often required. The zirconia sintered body is used as artificial teeth that are a substitution material in dental treatment, for example. With the artificial teeth, an appearance similar to that of natural teeth is required.

Patent Literature 1 discloses a multi-colored shaped body having layers arranged on top of one another for manufacture of dental restorations. The shaped body disclosed in Patent Literature 1 has (a) at least two successive and differently colored main layers, and (b) at least two differently colored intermediate layers between the at least two successive and differently colored main layers, wherein change in color between the intermediate layers takes place in a direction which is reverse to a direction of the change in color between the main layers.

PATENT LITERATURE 1: JP Patent Kokai Publication No. JP2008-68079A

SUMMARY

Technical Problem

The entire contents of disclosure of the above mentioned Patent Literature 1 are to be incorporated herein by reference. The following analysis is given from the perspective of the present invention.

As the shaped body disclosed in Patent Literature 1, in case where layers of different colors are merely laminated, entire change in color appears in stages (like stairs). That is, smooth gradation (color changes like a slope) can not be obtained. In particular, in the shaped body disclosed in Patent Literature 1, two intermediate layers are arranged between adjacent main layers. The direction of the change in color between these two intermediate layers is reversed to that of the entire change in color. Therefore, according to the shaped body disclosed in Patent Literature 1, natural gradation can not be realized.

Further, in a method disclosed in Patent Literature 1, in a case where the product is made of four colored main layers, for example, at least eight layers of the main layers and intermediate layers must be laminated. Therefore, the method disclosed in Patent Literature 1 needs much works and thus time costs.

According to a first aspect of the present invention, 1. a method for preparing a zirconia composition is provided, the method comprising: preparing a plurality of powders adapted to form a lamination of layers of the plurality of powders containing zirconia, a stabilizer(s) suppressing phase transition of zirconia and a pigment(s) at respective different pigment content ratios; and laminating layers of the plurality of powders for lamination in a mold. In the laminating step, the mold is vibrated after at least two layers of the powders for lamination are charged into the mold.

According to a second aspect of the present invention, a method for preparing a zirconia composition is provided, the method comprising; preparing a low addition ratio powder and a high addition ratio powder each containing zirconia, a stabilizer(s) suppressing phase transition of zirconia and a pigment(s), the low addition ratio powder and the high addition ratio powder differing in pigment content ratios from one another; mixing the low addition ratio powder and the high addition ratio powder to form at least one lamination powder; and laminating at least two out of the low addition ratio powder, high addition ratio powder and the lamination powder into the mold.

According to a third aspect of the present invention, a method for preparing a zirconia pre-sintered body (may be termed "calcined body") is provided, the method comprising the method for preparing the zirconia composition according to the present invention, and firing the composition at 800° C. to 1200° C.

According to a fourth aspect of the present invention, a method for preparing a zirconia sintered body is provided, the method comprising the method for preparing the zirconia composition according to the present invention, and firing the composition at 1400° C. to 1600° C.

According to a fifth aspect of the present invention, a method for preparing a zirconia sintered body is provided, the method comprising the method for preparing the zirconia pre-sintered body according to the present invention, and firing the pre-sintered body at 1400° C. to 1600° C.

According to a sixth aspect of the present invention, a zirconia sintered body is provided, which is manufactured by the method according the present invention.

According to a seventh aspect of the present invention, a zirconia pre-sintered body is provided, which is manufactured by the method according the present invention.

According to an eighth aspect of the present invention, a zirconia composition is provided, which is manufactured by the method according the present invention According to a ninth aspect of the present invention, a dental prosthesis is provided, which is obtained by milling, grinding and/or cutting the pre-sintered body according to the present invention and subsequently sintering the pre-sintered body.

The present invention has at least one of the following advantageous effects.

According to the present invention, a zirconia sintered body having natural gradation can be obtained.

The zirconia sintered body, described above, can be obtained from the composition as well as the pre-sintered body according to the present invention.

MODES

Figure 1:
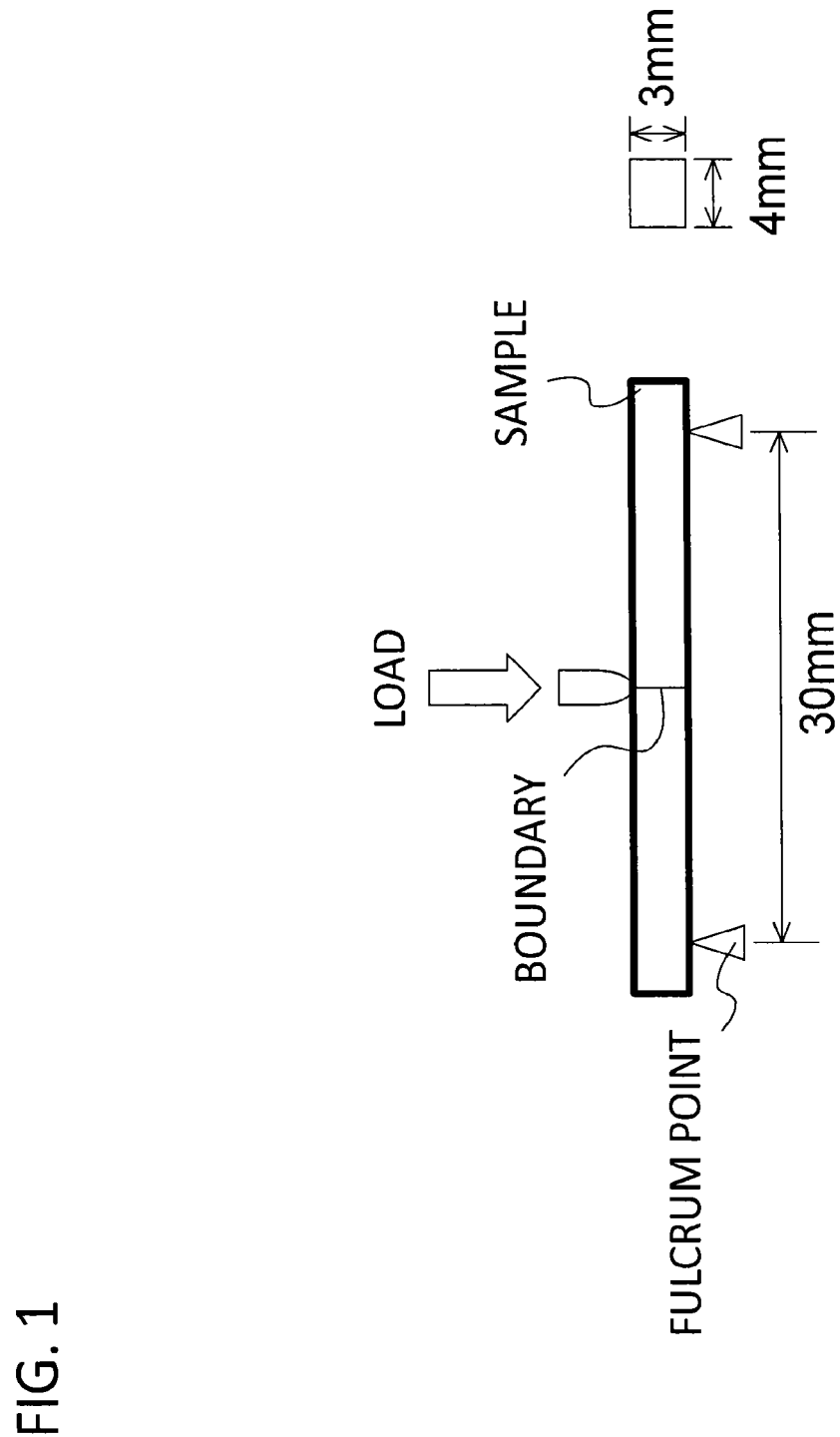
FIG. 1 is a schematic view for illustrating a three-point bending test method.

Preferred modes of the above respective aspects are now shown.

According to a preferred mode of the first aspect, in the laminating step, the mold is vibrated each time one powder for lamination is charged into the mold.

According to a preferred mode of the second aspect, in the laminating step, the mold is vibrated after charging at least two powders into the mold.

According to a preferred mode of the second aspect, in the mixing step, two or more powders for lamination with different mixing ratios of the low addition ratio powder and the high addition ratio powder are prepared. In the laminating step, the powders are laminated one on another so that the contents of the low addition ratio powder and the high addition ratio powder are varied in order.

According to a preferred mode of the first and second aspects, in the laminating step, after charging one powder into the mold, an upper surface of the powder is made flat.

According to a preferred mode of the first and second aspects, in the laminating step, the powders are laminated so that the pigment contents in the powders are varied in order.

According to a preferred mode of the sixth aspect, when the zirconia sintered body is prepared by sintering the zirconia composition, a flexural strength of the zirconia sintered body pursuant to JISR1601 is not less than 1100 MPa as measured with a load point of a three-point bending test aligned with a position of an interlayer boundary of lamination of the zirconia powders, the interlayer boundary traversing the test sample of the zirconia sintered body along a direction of load application.

According to a preferred mode of the sixth aspect, the flexural strength is not less than 1200 MPa.

According to a preferred mode of the sixth aspect, when a zirconia pre-sintered body is prepared by pre-sintering the zirconia composition at 800° C. to 1200° C., the flexural strength of the pre-sintered body as measured with a load point of a three-point bending test aligned with the interlayer boundary pursuant to JISR1601 is not less than 90% of the flexural strength of the zirconia pre-sintered body obtained on pre-sintering one composition of the zirconia powders alone at the same temperature as a pre-sintering temperature of the test sample, the interlayer boundary traversing the test sample of the pre-sintered body along a direction of load application.

According to a preferred mode of the sixth aspect, when the composition is pre-sintered at 800° C. to 1200° C. to form a zirconia pre-sintered body, the pre-sintered body is shaped to a form of a rectangular parallelepiped 50 mm in width[length], 10 mm in height and 5 mm in depth[thickness] as a test sample, and two surfaces of the test sample of 50 mm in width and 5 mm in depth are taken to be bottom surfaces; boundary surfaces formed by lamination of the zirconia powders then extending in the same direction as the bottom surfaces, the test sample is fired at 1500° C. for two hours, and the test sample is placed on a ground with one of the two bottom surfaces that has been deformed to a concave shape directed downwards, (a maximum gap between the deformed concave bottom surface and a ground surface)/(distance between portions of the test sample contacting the ground surface along the widthwise direction)×100 is 0.15 or less.

According to a preferred mode of the sixth aspect, it is assumed that, on a straight line extending in a first direction from one end to an opposite end, a chromaticity (L*, a*, b*) in an L*a*b* color chromaticity diagram at a first point in a domain from one end to up to 25% of a total length of the straight line is (L1, a1, b1), and a chromaticity (L*, a*, b*) in the L*a*b* color chromaticity diagram at a second point in a domain from the opposite end to up to 25% of the total length of the straight line is (L2, a2, b2). Then, L1 is not less than 58.0 and not larger than 76.0, a1 is not less than −1.6 and not larger than 7.6, b1 is not less than 5.5 and not larger than 26.7, L2 is not less than 71.8 and not larger than 84.2, a2 is not less than −2.1 and not larger than 1.8, b2 is not less than 1.9 and not larger than 16.0, L1<L2, a1>a2, b1>b2, increasing or decreasing tendency of the chromaticity in the L*a*b* color chromaticity diagram not being changed.

According to a preferred mode of the sixth aspect, there is no domain on the straight line interconnecting the first and second points where the L* value decreases by not less than unity (one) from a first point towards a second point. Also, there is no domain where the value of a* increases by not less than unity from the first point towards the second point, while there is no domain where the value of b* increases by not less than unity from the first point towards the second point.

According to a preferred mode of the sixth aspect, it is assumed that, on the straight line interconnecting the first and second points, the chromaticity (L*, a*, b*) in the L*a*b* color chromaticity diagram at a third point intermediate between the first and second points is (L3, a3, b3). Then, L3 is not less than 62.5 and not larger than 80.5, a3 is not less than −1.8 and not larger than 5.5, b3 is not less than 4.8 and not larger than 21.8, L1<L3<L2, a1>a3>a2 and b1>b3>b2.

According to a preferred mode of the sixth aspect, it is assumed that, on the straight line interconnecting the first and second points, the chromaticity (L*, a*, b*) in the L*a*b* color chromaticity diagram at a fourth point intermediate between the third and second points is (L4, a4, b4). Then, L4 is not less than 69.1 and not larger than 82.3, a4 is not less than −2.1 and not larger than 1.8, b4 is not less than 3.5 and not larger than 16.2, L1<L3<L4<L2, a1>a3>a4>a2 and b1>b3>b4>b2.

According to a preferred mode of the sixth aspect, the third point is at a distance from the one end equal to 45% of the total length, the fourth point is at a distance from the one end equal to 55% of the total length.

According to a preferred mode of the sixth aspect, the difference between the L* values of two neighboring ones of a first point, a third point, a fourth point and a second point is ΔL*, the difference between the values of a* of two neighboring points is Δa*, the difference between the values of b* of two neighboring points is Δb* and the ΔE*ab is calculated from the equation 1 shown below. Then, ΔE*ab between the first and third points is not less than 3.7 and not larger than 14.3, ΔE*ab between the third and fourth points is not less than 1.8 and not larger than 10.5 and ΔE*ab between the fourth and second points is not less than 1.0 and not larger than 9.0

$$\Delta E^*ab = \sqrt{(\Delta L^*)^2 + (\Delta a^*)^2 + (\Delta b^*)^2}$$ [Equation 1]

According to a preferred mode of the sixth aspect, it is assumed that, on the straight line interconnecting the first and second points, the chromaticity (L*a*b*) in the L*a*b* color chromaticity diagram of the third point located intermediate between the first and second points is (L3, a3, b3). Then L3 is not less than 69.1 and not larger than 82.3, a3 is not less than −2.1 and not larger than 1.8, b3 is not less than 3.5 and not larger than 16.2, L1<L3<L2, a1>a3>a2 and b1>b3>b2.

According to a preferred mode of the sixth aspect, the color is changed in the first direction extending from one end to the opposite end. On the straight line extending from the one end to the opposite end, increasing or decreasing tendency for the chromaticity in the L*a*b* color chromaticity diagram is not changed.

According to a preferred mode of the sixth aspect, on the straight line interconnecting the one end and the opposite end, the L* value tends to increase, while the a* value as well as the b* value tends to decrease, from the first point towards the second point.

According to a preferred mode of the sixth aspect, the distance from the one end to the opposite end is 5 mm to 18 mm.

According to a preferred mode of the sixth aspect, there is no color change along a second direction perpendicular to the first direction.

According to a preferred mode of the sixth aspect, it is assumed that, at two points on a straight line extending in the second direction, the difference between the L* values at two points is ΔL*, the difference between the a* values at the two points is Δa*, the difference between the b* values at the two points is Δb* and ΔE*ab is calculated from the equation 1. Then, E*ab is less than unity.

According to a preferred mode of the sixth aspect, flexural strength as measured pursuant to JISR1601 is not less than 1000 MPa.

According to a preferred mode of the sixth aspect, fracture toughness as measured pursuant to JISR1607 is not less than 3.5 MPa·m$^{1/2}$.

According to a preferred mode of the sixth aspect, in an X-ray diffraction pattern of a zirconia sintered body following a hydrothermal treatment test at 180° C. and 1 MPa for five hours, a ratio of a height of a peak existing in the vicinity of a [11-1] peak ascribable to a monoclinic crystal in the vicinity of 28° of 2θ to a height of a peak existing in the vicinity of a [111] peak ascribable to a tetragonal crystal in the vicinity of 30° of 2θ not larger than unity.

According to a preferred mode of the seventh aspect, a flexural strength of a test sample of the zirconia pre-sintered body, measured pursuant to JISR1601, is not less than 90% of a flexural strength of a comparative zirconia pre-sintered body; the comparative zirconia pre-sintered body being formed by pre-sintering one of the zirconia powders alone at the same temperature as a pre-sintering temperature of the test sample; the flexural strength being measured under a condition that a load point of a three-point bending test is positioned at a position of an interlayer boundary of the zirconia powders, the interlayer boundary traversing the test sample of the sintered body along a direction of load application.

According to a preferred mode of the seventh aspect, when the pre-sintered body is shaped to a form of a rectangular parallelepiped 50 mm in width[length], 10 mm in height and 5 mm in depth[thickness] as a test sample, two surfaces of the test sample of 50 mm in width and 5 mm in depth, are taken to be bottom surfaces; boundary surfaces formed by lamination of the zirconia powders extending in the same direction as the bottom surfaces; the test sample is fired at 1500° C. for two hours; and the test sample is placed on a ground with one of the two bottom surfaces that has been deformed to a concave shape directed downwards; (a maximum gap between the deformed concave bottom surface and a ground surface)/(distance between portions of the test sample contacting the ground surface along a widthwise direction)×100 is 0.15 or less.

According to a preferred mode of the ninth aspect, milling, grinding and/or cutting is performed by a CAD/CAM system.

According to the present invention, if the zirconia sintered body has a shape of a crown, preferably the 'one end' and the 'opposite end' denote one point in an end on an incisal side and one point in an end on a root side. The one point may be a point on an end face or on a cross-sectional face. The point located in a domain within 25% of the total length from the one end or the opposite end denotes a point that spans a distance equivalent to 10% of a crown height apart from the one end or the opposite end.

In case where the zirconia sintered body has a shape of a disc or a hexahedron such as a rectangular parallelepiped, the 'one end' or the 'opposite end' preferably denotes a point on the upper surface or the lower surface (bottom surface). The one point may be a point on an end face or on a cross-sectional face. The point located in a domain from one end or the opposite end to a point corresponding to 25% of the total length denotes a point that spans a distance equivalent to 10% of the thickness of the disc or the hexahedron apart from the one end or the opposite end.

According to the present invention, the 'first direction extending from one end to the opposite end' denotes a direction along which the color changes. As an example, the first direction is preferably the direction of laminating powders in a fabrication method as later explained. If, for example, the zirconia sintered body has the shape of a crown, the first direction is preferably a direction interconnecting the incisal side and the root side.

The zirconia sintered body of the present invention will now be explained. The zirconia sintered body of the present invention is mainly composed of partially stabilized zirconia crystal grains sintered together, and includes partially stabilized zirconia as a matrix phase. In the zirconia sintered body of the present invention, the principal crystal phase of zirconia is tetragonal crystal or tetragonal crystal plus cubical crystal. Preferably, the zirconia sintered body is substantially free of the monoclinic crystal in the state prior to treatment with hydrothermal testing as later explained.

The zirconia sintered body encompasses not only one obtained on sintering the shaped zirconia particles together at normal pressure or under a non-pressurizing state but also that obtained by subjecting the sintered body to high temperature compression such as hot isostatic pressing (HIP) for compacting and densification.

The zirconia sintered body according to the present invention contains zirconia and its stabilizer(s). The stabilizer(s) suppresses phase transition of the zirconia of the tetragonal system to the monoclinic system. By suppressing the phase transition, it is possible to elevate strength, durability as well as dimensional stability. As the stabilizer(s), oxides such as calcium oxide (CaO), magnesium oxide (MgO), yttrium oxide ($Y_2O_3$), referred to below as 'yttria', and cerium oxide (CeO$_2$) may be given, for example. Preferably, such an amount of the stabilizer(s) that will cause zirconia particles of the tetragonal system to be partially stabilized is added. For example, if yttria is used as the stabilizer, the content of yttria is preferably 2.5 mol % to 5 mol %, more preferably 3 mol % to 4.5 mol % and further preferably 3.5 mol % to 4.5 mol % relative to the total of mols of zirconia and yttria summed together. If the content of the stabilizer(s) is too high, the flexural strength as well as the fracture toughness is lowered, even though the phase transition is suppressed. If conversely the content of the stabilizer is too low, suppression of the progress of phase transition is insufficient even though the deterioration of the flexural strength as well as fracture toughness could be suppressed. By the way, zirconia of the tetragonal system, partially stabilized by addition of the stabilizer, is termed partially stabilized zirconia (PSZ).

Preferably, the zirconia sintered body of the present invention contains aluminum oxide Al$_2$O$_3$ (alumina). Preferably, addition of aluminum oxide may improve strength. The content of aluminum oxide in the zirconia sintered body is preferably 0 mass % (no aluminum oxide content) to 0.3 mass % relative to the total mass of zirconia and the stabilizer. If the aluminum oxide content exceeds 0.3 mass %, the sintered body is deteriorated in transparency. [Translator's Note: "mass %" is substantially equivalent to "weight %".]

Preferably, the zirconia sintered body of the present invention contains titanium oxide TiO$_2$ (titania). The content of titanium oxide may promote grain growth. The content of titanium oxide in the zirconia sintered body is preferably 0 mass % (no titanium oxide) to 0.6 mass % relative to the total mass of zirconia and the stabilizer. If the titanium oxide content exceeds 0.6 mass %, strength is deteriorated.

In the zirconia sintered body of the present invention, the content of silicon oxide SiO$_2$ (silica) is preferably not larger than 0.1 mass % relative to the total mass of zirconia and the stabilizer. The zirconia sintered body preferably substantially contains no silicon oxide. The reason is that, if silicon oxide is contained, the zirconia sintered body is deteriorated in transparency. By the phrase 'substantially contains no silicon oxide' is meant that silicon oxide is contained within a range that does not affect the property or the characteristic of the present invention, or that silicon oxide is contained in an amount not exceeding the level of the content of impurities. It is not necessarily meant that the silicon oxide content is below the limit of detection.

The zirconia sintered body of the present invention may contain a pigment(s) for coloring. If the zirconia sintered body is applied as a dental material, chromium oxide (Cr$_2$O$_3$), erbium oxide (Er$_2$O$_3$), iron oxide (Fe$_2$O$_3$), praseodymium oxide (Pr$_6$O$_{11}$) and so forth may be used as pigment(s). Such a pigment(s) may be used also in combination. The contents of the pigment(s) may partially be differentiated.

For example, if the zirconia sintered body, used as a dental material, contains chromium oxide, the partial content of chromium oxide in a local portion containing chromium oxide is preferably not larger than 0.001 mass % relative to the total mass of the zirconia and the stabilizer. If the zirconia sintered body, used as the dental material, contains erbium oxide, the partial content of erbium oxide in the local portion containing erbium oxide is preferably not larger than 2 mass % relative to the total mass of the zirconia and the stabilizer. If the zirconia sintered body, used as the dental material, contains iron oxide, the partial content of iron oxide in a local portion containing iron oxide is preferably not larger than 0.1 mass % relative to the total mass of the zirconia and the stabilizer. If the zirconia sintered body, used as the dental material, contains praseodymium oxide, the partial content of praseodymium oxide in a local portion containing praseodymium oxide is preferably not larger than 0.1 mass % relative to the total mass of the zirconia and the stabilizer.

In an X-ray diffraction pattern, as measured using CuKα rays, of the zirconia sintered body, following the sintering and before a hydrothermal treatment test, a sort of degradation acceleration test, as later explained, the ratio of height of a peak (referred to below as a 'second peak') existing in the vicinity of a [11-1] peak derived from the monoclinic crystal in the vicinity of 28° of 2θ to the height of a peak (referred to below as a 'first peak') existing in the vicinity of a [111] peak derived from the tetragonal crystal in the vicinity of 30° of 2θ is preferably not larger than 0.1 and more preferably not larger than 0.05. By the way, the above ratio, which is 'the height of the second peak/the height of the first peak', is referred to below as a 'peak ratio of the monoclinic crystal'.

In the zirconia sintered body of the present invention, progress of the phase transition from the tetragonal crystal to the monoclinic crystal is suppressed even though the hydrothermal treatment test is carried out. For example, in case the zirconia sintered body is hydrothermally treated at 180° C. and 1 MPa for 5 hours, the peak ratio of the monoclinic crystal in the X-ray diffraction pattern, as measured with CuKα rays on the surface of the hydrothermally treated zirconia sintered body, is preferably not larger than unity, more preferably not larger than 0.8, more preferably not larger than 0.7 and further preferably not larger than 0.6.

In the present description, the 'hydrothermal treatment test' denotes a test pursuant to ISO13356, in which the condition prescribed in ISO13356 is '134° C., 0.2 MPa, 5 hours'. In the present invention, to make the test condition more severe, the former two conditions are set at '180° C., 1 MPa', and the test time is appropriately in accordance with a given objective. The hydrothermal treatment test is also termed a 'low temperature deterioration acceleration test' or a 'hydrothermal deterioration test'.

The flexural strength as measured pursuant to JISR1601 of the zirconia sintered body according to the present invention is preferably not less than 1000 MPa, more preferably not less than 1100 MPa and further preferably not less than 1200 MPa. It is noted that these values are those for the state of the sintered body that is not applied to the hydrothermal treatment test yet.

In the zirconia sintered body according to the present invention, the above mentioned flexural strength can be obtained in the three-point bending test even in a case where the load point is located at a position of the interlayer boundary (may be simply termed as "boundary" herein) in the fabrication method as later explained. FIG. 1 schematically depicts a three-point bending test. For example, in the test sample, the interlayer boundary, which is produced by laminating zirconia powders of different compositions, is disposed at the center of the length (the midpoint in a longitudinal direction) of the test sample. The boundary extends along a direction of load application (along a direction of the smallest cross-sectional area) to traverse the test sample. The load point in the three-point bending test is aligned with the position of the boundary. Even in case the flexural strength is measured by a test which imposes a load on the boundary, it is possible to obtain a strength comparable to that of the sintered body which is not of a laminated (multi-layered) structure, i.e., a sintered body free of the boundary. For example, in the sintered body according to the present invention, the flexural strength measured as load is applied to the interlayer boundary is preferably not less than 90% and more preferably not less than 95% of the flexural strength of a local portion other than the boundary, (for example, the flexural strength of a pre-sintered body prepared from a non-laminated composition, under comparable conditions, e.g., same pre-sintering temperature pre-sintering time).

The fracture toughness of the zirconia sintered body according to the present invention, as measured pursuant to JISR1607, is preferably not less than 3.5 MPa·m$^{1/2}$, more preferably not less than 3.8 MPa·m$^{1/2}$, more preferably not less than 4 MPa·m$^{1/2}$ and further preferably not less than 4.2 MPa·m$^{1/2}$. By the way, these values are those obtained in the state prior to performing the hydrothermal treatment test.

In a test for measuring the fracture toughness of the zirconia sintered body, according to the present invention, even in case a load point is on the portion corresponding to the interlayer boundary of the layers in the fabrication method as later explained, the above mentioned value of the fracture toughness may be obtained. For example, in the test sample, the boundary produced by laminating zirconia powders of different compositions is located at the center of the test sample (the midpoint in the longitudinal direction). The boundary extends along the load applying direction (along a direction with the smallest [cross-sectional] area direction) to traverse the test sample. The position of a diamond pressing tip used in the measurement test is aligned with the boundary. Even in case where the fracture toughness is measured by a test which imposes a load on the boundary, in this manner, it is possible to obtain a fracture toughness comparable to that for a non-laminated, that is, boundary-free, sintered body.

It is desirable for the zirconia sintered body of the present invention that the above values are satisfied for every item of the peak ratio of the monoclinic crystal after the hydrothermal treatment, flexural strength and the fracture toughness. For example, with the zirconia sintered body of the present invention, preferably the peak ratio of the monoclinic crystal after the hydrothermal treatment is not larger than unity (one), the fracture toughness is not less than 3.5 MPa·m$^{1/2}$, and the flexural strength is not less than 1000 MPa. More preferably, with the zirconia sintered body of the present invention, the peak ratio of the monoclinic crystal after the hydrothermal treatment is not larger than 0.6, the fracture toughness is not less than 4 MPa·m$^{1/2}$, while the flexural strength is not less than 1000 MPa.

Figure 2:
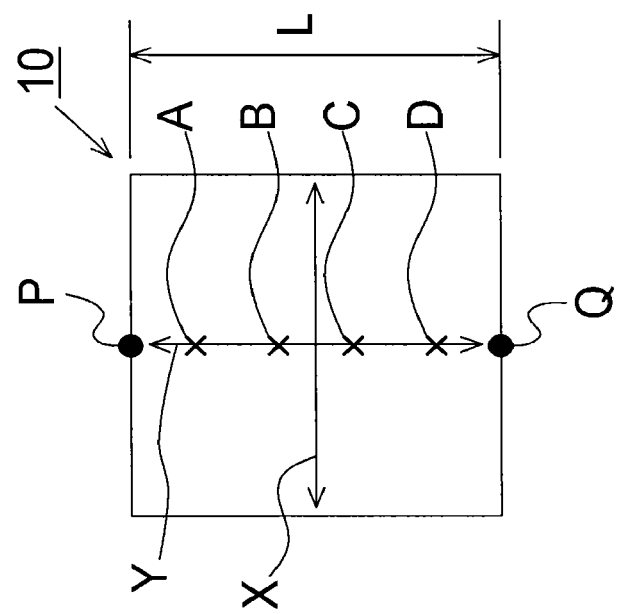
FIG. 2 is a schematic view of a zirconia sintered body.

In case where the zirconia sintered body according to the present invention is colored, in particular the zirconia sintered body gradually changes in color, i.e., presents color gradation, in one direction, it is desirable that there is a direction along which the color is substantially not changed. FIG. 2 depicts a schematic illustration for the zirconia sintered body. In the zirconia sintered body 10, shown in FIG. 2, it is desirable that the color is substantially not changed in a first direction X. It is assumed that, between optional two points on a straight line extending in the first direction X, the differences in chromaticity values L*, a*, b*, representing the chromaticity values in the L*a*b* color chromaticity diagram (JISZ8729), are denoted ΔL*, Δa* and Δb* and ΔE*ab is calculated in accordance with the following equation, ΔE*ab is preferably less than unity (one) and more preferably less than 0.5.

$$\Delta E^*ab = \sqrt{(\Delta L^*)^2 + (\Delta a^*)^2 + (\Delta b^*)^2}$$ [Equation 2]

In case where the zirconia sintered body of the present invention is colored, it is desirable that the sintered body changes in color, that is, presents color gradation, from one end to the opposite end. On a straight line extending in the second direction Y from one end P to the opposite end Q of the zirconia sintered body 10 shown in FIG. 2, the increasing or decreasing tendency of the L* value, a* value and b* value is desirably not changed in the reverse direction. Viz., if, on the straight line extending from the one end P to the opposite end Q, the L* value tends to increase, it is desirable that there exists no domain where the L* value substantially decreases. For example, if, on the straight line extending from the one end P to the opposite end Q, the L* value tends to increase, it is desirable that there exists no domain where the L* value decreases by not less than unity, while it is more desirable that there exists no domain where the L* value decreases by not less than 0.5. If, on the straight line extending from the one end P to the opposite end Q, the a* value tends to decrease, it is desirable that there exists no domain where the a* value substantially increases. For example, if, on the straight line extending from the one end P to the opposite end Q, the a* value tends to decrease, it is desirable that there exists no domain where the a* value increases by unity or more, while it is more desirable that there exists no domain where the a* value increases by 0.5 or more. In addition, if, on the straight line extending from the one end P to the opposite end Q, the b* value tends to decrease, it is desirable that there exists no domain where the b* value substantially increases. For example, if, on the straight line extending from the one end P to the opposite end Q, the b* value tends to decrease, it is desirable that there exists no domain where the b* value increases by unity or more, while it is more desirable that there exists no domain where the a* value increases by 0.5 or more.

As for the color change direction in the zirconia sintered body 10, if the L* value tends to increase from the one end P to the opposite end Q, it is preferred that the a* and b* values tend to decrease. If, for example, the zirconia sintered body 10 is used as a dental prosthetic material, it is preferred that the color changes from pale yellow, pale orange or thin brown to white from the one end P to the opposite end Q.

Referring to FIG. 2, points on the straight line interconnecting one point P and the opposite end Q are labeled a first point A, a second point B, a third point C and a fourth point D, looking from the end P in order. For example, if the zirconia sintered body 10 is used as dental prosthesis, the first point A is desirably in a domain of 25% to 45% of a length from the one point P to the opposite end Q (referred to below as 'total length') as measured from the one end P. The second point B is desirably in a domain from a site spaced a distance equal to 30% of the total length apart from the one point P up to a point of 70% from the one end P. The fourth point D is desirably in a domain of 25% to 45% of the total length from the opposite end Q. The third point C is desirably in a domain from a site spaced a distance equal to 30% of the total length apart from the opposite point Q up to a point of 70% of the total length from the opposite end Q.

The chromaticity (L*, a*, b*) of the zirconia sintered body 10 in the L*a*b* color chromaticity diagram (JISZ8729) at the first point A, second point B, third point C and the fourth point D is expressed as (L1, a1, b1), (L2, a2, b2), (L3, a3, b3), (L4, a4, b4), respectively. It is desirable in this case that the following large/small relationship. By the way, the chromaticity of each point may be found by preparing a zirconia sintered body of the sole composition corresponding to each point and measuring the chromaticity of each such zirconia sintered body.

$$L1 < L2 < L3 < L4$$

$$a1 > a2 > a3 > a4$$

$$b1 > b2 > b3 > b4$$

In case where the zirconia sintered body is applied to a dental material, L1 is desirably not less than 58.0 and not larger than 76.0. L2 is desirably not less than 62.5 and not larger than 80.5. L3 is desirably not less than 69.1 and not larger than 82.3. L4 is desirably not less than 71.8 and not larger than 84.2.

In case where the zirconia sintered body is applied to a dental material, a1 is desirably not less than −1.6 and not larger than 7.6. a2 is desirably not less than −1.8 and not larger than 5.5. a3 is desirably not less than −2.1 and not larger than 1.6. a4 is desirably not less than −2.1 and not larger than 1.8.

In case where the zirconia sintered body is applied to a dental material, b1 is desirably not less than 5.5 and not larger than 26.7. b2 is desirably not less than 4.8 and not larger than 21.8. b3 is desirably not less than 3.5 and not larger than 16.2. b4 is desirably not less than 1.9 and not larger than 16.0.

In case where the zirconia sintered body is applied to a dental material, preferably L1 is not less than 60.9 and not larger than 72.5, a1 is not less than 0.2 and not larger than 5.9, b1 is not less than 11.5 and not larger than 24.9, L4 is not less than 72.2 and not larger than 79.2, a4 is not less than −1.2 and not larger than 1.7, b4 is not less than 6.0 and not larger than 15.8. More preferably, L1 is not less than 63.8 and not larger than 68.9, a1 is not less than 2.0 and not larger than 4.1, b1 is not less than 17.5 and not larger than 23.4, L4 is not less than 72.5 and not larger than 74.1, a4 is not less than −0.2 and not larger than 1.6, b4 is not less than 10.1 and not larger than 15.6. This allows matching to the average color tone of teeth.

The color difference ΔE*ab between two neighboring points may be expressed by the following equation. ΔL* is the difference between the L* values of two neighboring layers, such as (L1-L2). Δa* is the difference between the a* values of two neighboring layers, such as (a1-a2). Δb* is the difference between the b* values of two neighboring layers, such as (b1-b2). If the color difference between the first point A and the second point B is ΔE*ab1, that between the second point B and the third point C is ΔE*ab2 and that between the third point C and the fourth point D is ΔE*ab3, and the above mentioned relationship holds as to the chromaticity of each of the first point A, second point B, third point C and the fourth point D, then ΔE*ab1, for example, is desirably not less than 3.7 and not larger than 14.3. ΔE*ab2 is desirably not less than 1.8 and not larger than 17.9. ΔE*ab3 is desirably not less than 1.0 and not larger than 9.0. This can reproduce color changes similar to those of a natural tooth.

$$\Delta E^{*}ab = \sqrt{(\Delta L^{*})^{2} + (\Delta a^{*})^{2} + (\Delta b^{*})^{2}} \quad \text{[Equation 3]}$$

Assumed that the color difference between the first point A and the fourth point D is ΔE*ab4, and the above mentioned relationship holds as to the chromaticity of each of the first point A, second point B, third point C and the fourth point D, then ΔE*ab4, for example, is desirably not larger than 36. A value obtained by deducting the color difference ΔE*ab4 between the first point A and the fourth point D from the sum of the color difference ΔE*ab1 between the first point A and the second point B, color difference ΔE*ab2 between the second point B and the third point C and the color difference ΔE*ab3 between the third point C and the fourth point D is desirably not larger than unity. This allows representing natural changes in color.

In a case where continuous changes in b* value in the L*a*b* color chromaticity diagram (JISZ8729) along a straight line traversing the layers of the powders of respective different compositions (see the fabrication method below) as intersecting the interlayer boundary, that is, along a second direction Y shown in FIG. 2, are measured, it is preferred that, even in a direction traversing the layers, the b* value is not constant and shows a tendency to increase or decrease moderately. It is moreover preferred that, even if in a direction traversing the interlayer boundary portion, the b* value does not increase or decrease acutely. The changes in the b* value can be measured using e.g., a two-dimensional colorimeter manufactured and sold by PaPaLaB Co. Ltd. In measurement, the interval between neighboring measurement points may be set to 13 μm, as an example.

If the zirconia sintered body according to the present invention is applied as a dental material, the chromaticity of the fourth point D is in the above range, a zirconia sintered body is prepared from solely the composition corresponding to the fourth point, and both surfaces of the sintered body are polished to a mirror surface to provide a sample of 0.5 mm in thickness, the optical transmittance of the so prepared sample, as measured pursuant to JISK7361, is desirably not less than 27%. If the chromaticity of the first point A is in the above range, a zirconia sintered body is prepared from solely the composition corresponding to the first point, and both surfaces of the sintered body are polished to a mirror surface to a sample of 0.5 mm in thickness, the optical transmittance of the so prepared sample, as measured pursuant to JISK7361, is desirably not less than 10%.

In a case where the zirconia sintered body 10 of the present invention is applied to the dental material, it is desirable that a length L of the zirconia sintered body 10 in a first direction Y satisfies a length corresponding to at least an exposed portion of a natural tooth. For example, the length L of the zirconia sintered body 10 is preferably 5 mm to 18 mm.

The composition as well as the pre-sintered body for the preparation of the zirconia sintered body of the present invention will now be explained. The composition as well as the pre-sintered body is a precursor (partly-finished product) of the zirconia sintered body of the present invention. The pre-sintered body is obtained on firing, that is, pre-sintering (may be termed "calcining", too) at a temperature below the sintering temperature. The pre-sintered body encompasses a shaped product. A dental prosthesis, such as a crown, obtained by milling, grinding and/or cutting a pre-sintered zirconia disc using the CAD/CAM (Computer-Sided Design/Computer-Aided Manufacturing) may be included in the pre-sintered body.

The composition as well as the pre-sintered body is prepared as zirconia powders of respective different compositions are laminated one on another.

Each of the composition and the pre-sintered body contains zirconia crystal powders, mainly of the monoclinic system, a stabilizer(s) and titanium oxide. An aluminum oxide may be contained in the composition, too. Preferably, aluminum oxide is αalumina.

The average particle size of zirconia powder (in granulated state) in the composition is preferably 20 μm to 40 μm.

As the stabilizer(s) contained in the composition as well as the pre-sintered body, oxides, such as calcium (CaO), magnesium oxide (MgO), yttria or cerium oxide ($CeO_2$) may be given. Preferably, the stabilizer(s) is added in such an amount as to allow the zirconia powder in the sintered body to be partially stabilized. If, for example, yttria is used as the stabilizer, the content of yttria is preferably 2.5 mol % to 4.5 mol %, more preferably 3 mol % to 4.5 mol % and further preferably 3.5 mol % to 4.5 mol %, relative to the total of mols of zirconia and yttria.

The content of aluminum oxide in the composition as well as the pre-sintered body is preferably 0 mass % (no aluminum oxide content) to 0.3 mass % relative to the total mass of the zirconia crystal particles and the stabilizer(s) in order to elevate the strength of the zirconia sintered body. If the content of aluminum oxide exceeds 0.3 mass %, transmittance of the zirconia sintered body is lowered.

The content of titanium oxide in the composition as well as the pre-sintered body is preferably 0 mass % (no titanium oxide content) to 0.6 mass % relative to the total mass of the zirconia crystal particles and the stabilizer(s) in order to promote growth of zirconia crystal grains. If the content of titanium oxide exceeds 0.6 mass %, strength of the zirconia sintered body is lowered.

The content of silicon oxide in the composition as well as the pre-sintered body is preferably 0.1 mass % or less relative to the total mass of the zirconia crystal particles and the stabilizer(s). Preferably, the composition as well as the pre-sintered body is substantially free of silicon oxide $SiO_2$ (silica). It is because the content of silicon oxide lowers the transmittance of the zirconia sintered body. By the phrase 'substantially free of silicon oxide' it is meant that silicon oxide is contained within a range not affecting the property or the characteristic of the present invention, or that silicon oxide is preferably contained in an amount not exceeding the level of the content of impurities. It is not necessarily meant that the silicon oxide content is to be lower than the limit of detection.

The composition as well as the pre-sintered body according to the present invention may contain a pigment(s) for coloring. If the zirconia sintered body, prepared from the composition or the pre-sintered body, is used as the dental material, chromium oxide ($Cr_2O_3$), erbium oxide ($Er_2O_3$), iron oxide ($Fe_2O_3$), praseodymium oxide ($Pr_6O_{11}$) and so forth may be used as pigments, either alone or in combination. The contents of the pigments may partially be differentiated.

If the shaped composition or the pre-sintered body in its entirety is divided into four layers, a local portion from the bottom end to 25% to 45% of the total thickness is a first layer, a local portion from the top of the first layer to 5% to 25% of the total thickness is a second layer, a local portion from the top of the second layer to 5% to 25% of the total thickness is a third layer and a local portion from the top of the third layer to an upper end, having a thickness corresponding to 25% to 45% of the total thickness, is a fourth layer, preferably the pigment content decreases from the first layer towards the fourth layer.

If a sintered body, prepared from the composition or the pre-sintered body, is used as a dental material, erbium oxide and iron oxide may be added as pigment(s). In this case, the content of erbium oxide and the content of iron oxide in the first layer relative to the total mass of the zirconia and the stabilizer are preferably 0.33 mass % to 0.52 mass % and 0.05 mass % to 0.12 mass %, respectively. The content of erbium oxide and the content of iron oxide in the second layer relative to the total mass of the zirconia and the stabilizer are preferably 0.26 mass % to 0.45 mass % and 0.04 mass % to 0.11 mass %, respectively. The content of erbium oxide and the content of iron oxide in the third layer relative to the total mass of the zirconia and the stabilizer are preferably 0.05 mass % to 0.24 mass % and 0.012 mass % to 0.08 mass %, respectively. The content of erbium oxide and the content of iron oxide in the fourth layer relative to the total mass of the zirconia and the stabilizer are preferably 0 mass % to 0.17 mass % and 0 mass % to 0.07 mass %, respectively. Preferably, the content of erbium oxide and the content of iron oxide decrease from the first layer towards the fourth layer in order.

If, for example, a sintered body prepared from a composition or a pre-sintered body is used as a dental material, erbium oxide, iron oxide and chromium oxide may be added as the pigments. If the sintered body prepared from the composition or the pre-sintered body is used as a dental material, it is preferred that, in the first layer, the content of erbium oxide, that of iron oxide and that of chromium oxide relative to the total mass of the zirconia and the stabilizer(s) are preferably 0.08 mass % to 0.37 mass %, 0.08 mass % to 0.15 mass % and 0.0008 mass % to 0.0012 mass %, respectively. In the second layer, it is preferred that the content of erbium oxide, that of iron oxide and that of chromium oxide relative to the total mass of the zirconia and the stabilizer(s) are preferably 0.06 mass % to 0.42 mass %, 0.06 mass % to 0.18 mass % and 0.0006 mass % to 0.001 mass %, respectively. In the third layer, it is preferred that the content of erbium oxide, that of iron oxide and that of chromium oxide relative to the total mass of the zirconia and the stabilizer(s) are preferably 0.06 mass % to 0.17 mass %, 0.018 mass % to 0.042 mass % and 0.0001 mass % to 0.0003 mass %, respectively. In the fourth layer, it is preferred that the content of erbium oxide, that of iron oxide and that of chromium oxide relative to the total mass of the zirconia and the stabilizer(s) are preferably 0 mass % to 0.12 mass %, 0 mass % to 0.001 mass % and 0 mass % to 0.0001 mass %, respectively. It is preferred that the content of erbium oxide, that of iron oxide and that of chromium oxide decrease from the first layer towards the fourth layer in order.

If, for example, a sintered body prepared from the composition or the pre-sintered body is used as a dental material, erbium oxide, iron oxide and praseodymium oxide may be added as the pigments. If the sintered body prepared from the composition or the pre-sintered body is used as a dental material, it is preferred that, in the first layer, the content of erbium oxide, that of iron oxide and that of praseodymium oxide relative to the total mass of the zirconia and the stabilizer(s) are preferably 0.08 mass % to 2.2 mass %, 0.003 mass % to 0.12 mass % and 0.003 mass % to 0.12 mass %, respectively. In the second layer, it is preferred that the content of erbium oxide, that of iron oxide and that of praseodymium oxide relative to the total mass of the zirconia and the stabilizer(s) are preferably 0.06 mass % to 1.9 mass %, 0.002 mass % to 0.11 mass % and 0.002 mass % to 0.11 mass %, respectively. In the third layer, it is preferred that the content of erbium oxide, that of iron oxide and that of praseodymium oxide relative to the total mass of the zirconia and the stabilizer(s) are preferably 0.018 mass % to 1 mass %, 0.008 mass % to 0.06 mass % and 0.0008 mass % to 0.06 mass %, respectively. In the fourth layer, it is preferred that the content of erbium oxide, that of iron oxide and that of praseodymium oxide relative to the total mass of the zirconia and the stabilizer(s) are preferably 0 mass % to 0.7 mass %, 0 mass % to 0.05 mass % and 0 mass % to 0.05 mass %, respectively. It is preferred that the content of erbium oxide, that of iron oxide and that of praseodymium oxide decrease from the first layer towards the fourth layer in order.

The content of the pigment(s) can be theoretically calculated from the amount of its addition with respect to the total mass of the zirconia and the stabilizer(s) and from the fabrication method.

The flexural strength of the pre-sintered body of the present invention, as measured in accordance with JISR1601, is preferably not less than 38 MPa, more preferably not less than 40 MPa and further preferably not less than 42 MPa.

With the pre-sintered body according to the present invention, even if, in the three-point bending test, the load point is located at an interlayer boundary portion produced by laminating zirconia powders of differing compositions (see the fabrication method below), the above mentioned flexural strength can be obtained. If the flexural strength is measured by the same bending test as that for the above mentioned sintered body, a flexural strength higher than that of the pre-sintered body prepared by simply laminating of powders (without applying vibration, for example) may be obtained. If the flexural strength is measured by a test which imposes load on the interlayer boundary, such strength comparable with that of a non-laminated, that is, interlayer boundary-free, pre-sintered body, may be obtained. With the pre-sintered body according to the present invention, the flexural strength measured under a load applied to the interlayer boundary is preferably not less than 90% and more preferably not less than 95% of the flexural strength as measured at a local portion other than the interlayer boundary, for example, the flexural strength of a pre-sintered body prepared from a non-laminated composition under comparable conditions, such as the same pre-sintering temperature and pre-sintering time.

Figure 3:
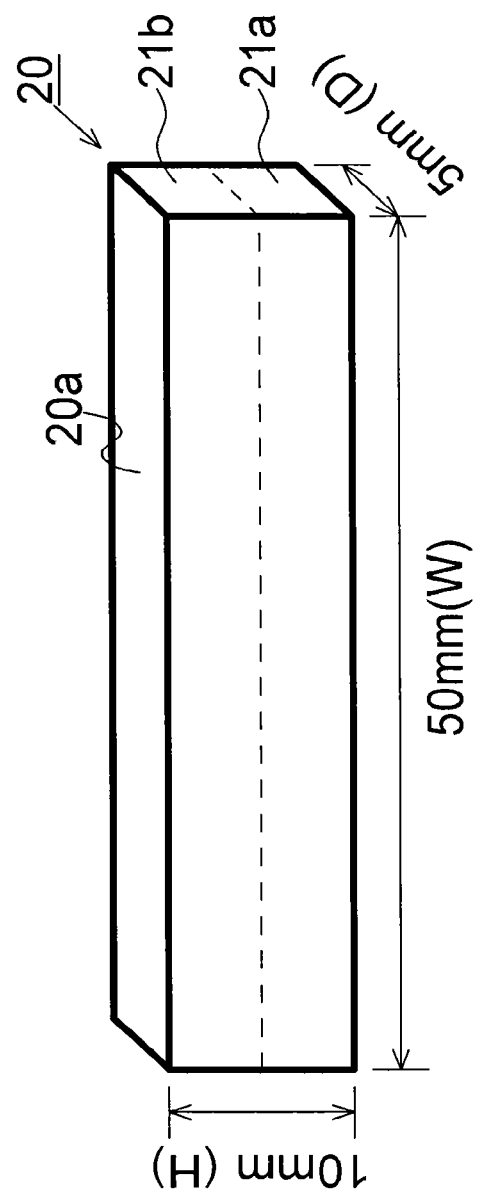
FIG. 3 is a schematic view showing a test sample used for measuring deformation at the time of sintering.
Figure 4:
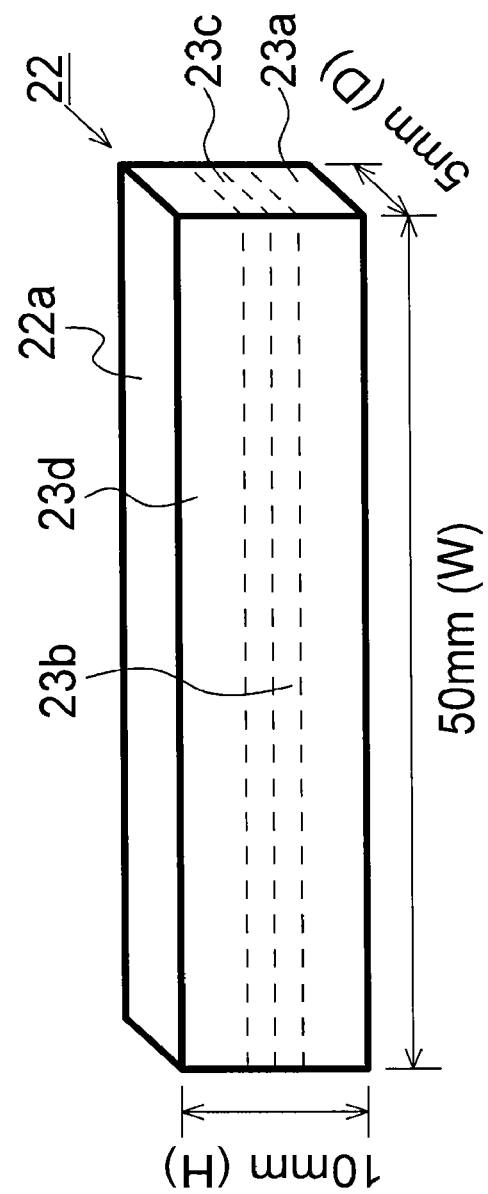
FIG. 4 is a schematic view showing a test sample used for measuring deformation at the time of sintering.
Figure 5:
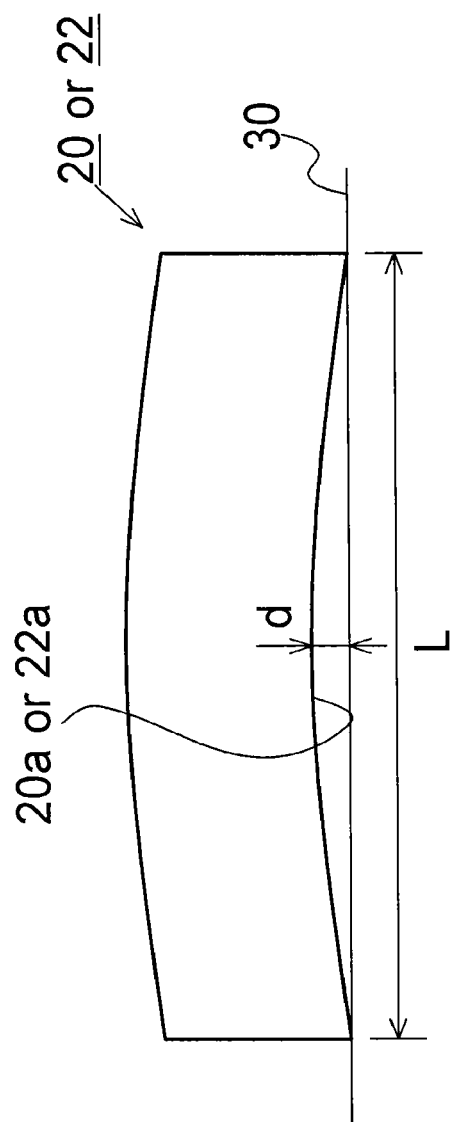
FIG. 5 is a schematic view for illustrating a method for measuring deformation.

With the composition and the pre-sintered body according to the present invention, even if heating is performed for pre-sintering or sintering, no layer exfoliation occurs at the boundary between lamination layers of zirconia powders of respective different compositions. In addition, the overall deformation can be suppressed. FIG. 3 and FIG. 4 depict schematic views of a test sample used for measuring the extent of the deformation at the time of sintering. FIG. 3 shows a schematic drawing of a two-layered lamination body. FIG. 4 shows a schematic drawing of a four-layered lamination body. FIG. 5 depicts a schematic view for illustrating a method for measuring the extent of the deformation. As an example, a plurality of zirconia powders, having respective different compositions, are laminated together to form a composition, and the composition is then fired (calcined) at 800° C. to 1200° C. for two hours to form a pre-sintered body. The pre-sintered body is then shaped by the CAD/CAM system to a rectangular parallelepiped which is 50 mm in width[length], 10 mm in height and 5 mm in depth[thickness], as shown in FIG. 3 and FIG. 4. This serves as a test sample. As an example, a test sample 20 that is a two-layered lamination body, shown in FIG. 3, has a first layer 21a and a second layer 21b. Each of the thickness of the first layer 21a and that of the second layer 21b accounts for 50% of the total thickness. A test sample 22 that is a four-layered lamination body, shown in FIG. 4, includes a first layer 23a, a second layer 23b, a third layer 23c and a fourth layer 23d. The thickness of the first layer 23a and that of the fourth layer 23d each account for 35% of the total thickness. The thickness of the second layer 23b and that of the third layer 23c each account for 15% of the total thickness. If, in each of the test samples 20, 22, the surface of 50 mm by 5 mm is supposed to be the bottom surface (upper or lower surface), each layer extends in the same direction as, preferably parallel to, the bottom surfaces 20a, 22a. That is, each interlayer boundary is parallel to the bottom surfaces 20a, 22a. If the test samples are fired at 1500° C. for two hours for sintering, the test samples are deformed so that the bottom surfaces 20a, 22a are flexed. The test samples 20, 22 are set on a flat surface (ground surface 30) with the concave surface side directed downwards. The width of each of the as-deformed test samples 20, 22, that is, a distance L between the ground contacting points (fulcrum points) along the width, is measured. On the other hand, a gap d at the largest portion between the bottom surfaces 20a, 22a deformed to the concave shape and the ground surface 30 is measured. The extent (amount) of the deformation is calculated as (d/L×100). The deformation is preferably not larger than 0.15, more preferably not larger than 0.1, more preferably not larger than 0.05 and further preferably not larger than 0.03.

Such a composition or a pre-sintered body, obtained on laminating zirconia powders of different compositions, is susceptible to deformation when subjected to sintering. With the composition or the pre-sintered body according to the present invention, the extent of the deformation can be made smaller than that in the composition or the pre-sintered body obtained on simple lamination. As a result, an end product can be improved in dimensional accuracy. The composition and the pre-sintered body according to the present invention can be applied to advantage to a dental prosthesis that may appreciably be different from person to person. By the way, a mixture layer presumed to have been formed on a boundary (interface) between neighboring (upper and lower) layers is not shown in FIG. 3 or in FIG. 4 for simplicity.

The composition of the present invention may be powder, a fluid obtained on adding powders to a solvent, or a shaped body obtained on shaping the powders to a preset shape. That is, the composition may be powdery, or paste-like or wet composition. (In other words, the composition may be present in a solvent or contain a solvent.) The composition may also contain an additive(s), such as a binder(s) and pigment(s). By the way, the mass of the solvent and the additive such as the binder is not taken into account in calculating the content ratio.

In case where the composition of the present invention is a shaped body, there is no limitation to the method of shaping. The composition may be shaped by e.g., pressing, injection molding or stereolithography (or opto-molding). It may also be shaped by multistage shaping (forming). For example, the composition of the present invention may be shaped by pressing followed by cold isostatic pressing (CIP).

The pre-sintered body according to the present invention can be obtained by firing the composition of the present invention at 800° C. to 1200° C. under normal atmospheric pressure.

The pre-sintered body of the present invention can be adapted to form the zirconia sintered body according to the present invention by being fired at 1350° C. to 1600° C. under normal atmospheric pressure.

The length of the composition and the pre-sintered body along its laminating (i.e., layer-stacking) direction (thickness) is preferably determined so as to realize a targeted length of the sintered body as sintering shrinkage is taken into account. When the sintered body prepared from the composition or the pre-sintered body is used as a dental material, as an example, the targeted length along the laminating direction of the sintered body is 5 mm to 18 mm, as an example, while the length (thickness) along the laminating direction of the composition or the pre-sintered body may be set at 10 mm to 26 mm.

An example of a fabrication method for the composition and the pre-sintered body as well as the sintered body according to the present invention will now be explained. Here, the method for gradually changing the color of the sintered body (color gradation) will also be explained.

Initially, zirconia and the stabilizer are wet-mixed together in water to form a slurry. Next, the slurry is then dried and granulated. The resulting granules are then pre-sintered to form primary powders.

If color gradation is to be imparted to the sintered body, the primary powders are divided into two groups. Then, a pigment(s) is added to at least one of the two groups of the primary powders to provide for difference in the ratio of pigment addition. For example, a pigment may be added to one of the groups, whereas no pigment may be added to the other. A powder (powder group) with a low addition ratio of a specified pigment is referred to below as "low addition ratio powder", while a powder (powder group) with a high addition ratio of the specified pigment is referred to below as "high addition ratio powder". The amount of pigment addition in the high addition ratio powder is preferably adapted to an addition ratio of a portion having darkest color in the sintered body. With regard to each powder, zirconia is mixed and pulverized in water to a desired particle size to form a zirconia slurry. Next, the slurries are dried and granulated to form secondary powders. In case of addition of additive(s) such as aluminum oxide, titanium oxide and the binder, they may be added at the time of preparation of the primary powders or at the time of preparation of the secondary powders.

A plurality of powders having respective different pigment contents are then prepared from the secondary powders of the low addition ratio powder and the high addition ratio powder. As an example, if the four-layered lamination composition and pre-sintered body are to be prepared, a first powder for the first layer may be made up of 100% of the high addition ratio powder without adding the low addition ratio powder. A second powder for the second layer may be prepared by mixing the low addition ratio powder and the high addition ratio powder at a mixing ratio of the low addition ratio powder to high addition ratio powder of 5:95 to 15:85. A third powder for the third layer may be prepared by mixing the low addition ratio powder and the high addition ratio powder at a mixing ratio of the low addition ratio powder to high addition ratio powder of 35:65 to 45:55. A fourth powder for the fourth layer may be prepared by mixing the low addition ratio powder and the high addition ratio powder at a mixing ratio of the low addition ratio powder to high addition ratio powder of 45:55 to 55:45. By way of alternative values of the mixing ratio, in preparing the above mentioned four-layered lamination composition and pre-sintered body, the first powder for the first layer may be made up of 100% of the high addition ratio powder without adding the low addition ratio powder. The second powder for the second layer may be prepared by mixing the low addition ratio powder and the high addition ratio powder at a mixing ratio of the low addition ratio powder to high addition ratio powder of 10:90 to 30:70. The third powder for the third layer may be prepared by mixing the low addition ratio powder and the high addition ratio powder at a mixing ratio of the low addition ratio powder to high addition ratio powder of 70:30 to 90:10. The fourth powder for the fourth layer may be made up of 100% of the low addition ratio powder without adding the high addition ratio powder.

In using the zirconia sintered body as the dental material, the difference between the mixing ratios for the second and third layers is preferably larger than that between the mixing ratios for the first and second layers as well as that between the mixing ratios for the third and fourth layers. By so doing, it is possible to reproduce color changes comparable to those of a natural tooth.

By adjusting the pigment contents in the respective layers, based on the two sorts of powders that present different colors in the sintered body, it is possible to realize natural changes in color (color gradation) by laminating the respective powders (stacking layers) in order.

If laminating is made for some other objective than coloring, the secondary powders may be divided into a number of groups corresponding to the number of the layers. A desired additive(s) may be added to each powder.

A plurality of powders having respective different pigment contents are then laminated in order. If desired to impart color gradation to the sintered body, it is preferred that the powders are laminated so that the ratio of addition of a particular pigment becomes higher or lower stepwise in the sequence of layering. Initially, powder(s) of the first layer is charged into a mold and an upper surface of the powder(s) of the first layer is made flat. As a way of making it flat the upper surface of the powder(s), vibrating the mold or leveling the upper surface of the powder(s) of the first layer may be adopted. It is preferred not to perform pressing until the totality of the layers has been laminated. The powder(s) of the second layer is then charged on top of the powder(s) of the first layer. The mold is then vibrated so that the vibration is transmitted to the powders in the mold. As a way of giving the vibration, a desired way, such as giving a mechanical vibration to the mold, vibrating (or swinging) the mold manually and striking the mold with a hammer, for example, may be suitably adopted. It is thought that, by so doing, the powder(s) of the first layer and that of the second layer are partially mixed together at a boundary between the powders of the first and second layers. The number of times as well as intensity of the vibrations and, in the case of mechanical vibrations, the frequency and amplitude of the vibration may be appropriately set, depending on the particle size, particle size distribution or the particle shape, so that mixing of the powders of the upper and lower layers will take place on the interlayer boundary. The upper surface of the powder(s) of the second layer is then made flat as in the case of the powder(s) of the first layer. The sequence of operations is repeated until all of the layers are laminated.

If the above mentioned four-layered composition and pre-sintered body are to be formed, the first powder(s) is charged to a predetermined thickness, such as to 25% to 45% of the overall thickness. At this time, the upper surface of the first powder(s) is made flat, but pressing is not performed. The second powder(s) is then charged on the first powder(s) to a predetermined thickness, such as to 5 to 25% of the overall thickness. The mold is then vibrated. It is presumed that this vibration forms a first boundary layer, which is a mixture of the first and second powders, at a boundary between an upper surface of the first powder(s) and a lower surface of the second powder(s). The upper surface of the second powder is then made flat. Pressing is not applied to the second powder before charging the third powder. The third powders are charged on the second powder to a predetermined thickness, for example, to 25% to 45% of the overall thickness. The mold is then vibrated. It is presumed that this vibration forms a second boundary layer, which is a mixture of the second and third powders, at a boundary between an upper surface of the second powder(s) and a lower surface of the third powder(s). The upper surface of the third powder(s) is then made flat. Pressing the third powder(s) is not performed before charging the fourth powder(s). The fourth powder(s) is charged on the third powder(s) to a predetermined thickness, for example, to 25% to 45% of the overall thickness. The mold is then vibrated. It is presumed that this vibration forms a third boundary layer, which is a mixture of the third and fourth powders, at a boundary between an upper surface of the third powder(s) and a lower surface of the fourth powder(s).

After laminating the entire layers, pressing is carried out to form a shaped product as the composition of the present invention. The shaped product may then be subjected to CIP.

It is thought that, by not applying pressing before charging powder(s) of the next layer, and by applying vibration each time each layer is charged, a boundary layer where powders of upper and lower layers are mixed can be formed between neighboring layers. This enhances adhesion tightness between neighboring layers in the sintered body. The extent or speed of shrinkage at the time of heating may be equalized with that of each layer to prevent layer exfoliation at the time of heating or irregular deformation of the sintered body from the targeted shape. In addition, since the color difference between neighboring layers may be moderated, color change can occur naturally along the laminating direction in the sintered body (color gradation can be created).

Moreover, in this method, there is no necessity to provide an intermediate layer between main layers. That is, when four main layers are to be laminated, it is only necessary to laminate only the four layers. Additionally, pressing is not needed for each layer. Accordingly, work and time can be significantly reduced, and thus manufacturing cost can be reduced.

In case where no pre-sintered body is fabricated, the composition is fired at 1400° C. to 1600° C. and preferably at 1450° C. to 1550° C. to sinter the zirconia powder(s) to fabricate the zirconia sintered body according to the present invention. Shaping to a desired shape may be performed in a stage of the shaped product.

In case where a pre-sintered body is fabricated, the composition is fired at 800° C. to 1200° C. to form a pre-sintered body. The pre-sintered body is then fired at 1400° C. to 1600° C., preferably 1450° C. to 1550° C. to sinter the zirconia powder to fabricate the zirconia sintered body according to the present invention. Shaping may be performed by milling, grinding and/or cutting etc. in a stage of the pre-sintered body or following the sintering. The shaping may be carried out with the CAD/CAM system.

The fabrication method for a dental prosthesis is similar to the above described fabrication method except that the pre-sintered or sintered body is shaped to the form of a crown.

In the above described exemplary embodiment, the composition, pre-sintered body and the sintered body, in the form of a four-layered lamination structure, has been shown and explained. However, the number of layers may be other than four. The composition, pre-sintered body or the sintered body may, as an example, be formed with two layers, namely the first and fourth layers. Alternatively, the composition, pre-sintered body or the sintered body may, as an example, be formed with three layers, namely the first, second and fourth layers. It is noted that FIG. 2 is only for facilitated explanation of the positional relationships and directions of respective points such that the shape and size are not limited to those shown in FIG. 2.

EXAMPLES

Examples 1 to 4

[Preparation of Composition, Pre-Sintered Body Sample and Sintered Body Sample]

A sintered body sample was fabricated from a composition prepared on laminating zirconia powders of respective different compositions and measurement was made of its flexural strength, chromaticity and extent of deformation.

Initially, a zirconia powder containing a stabilizer was prepared. 7.2 mass % (4 mol %) of yttria, as stabilizer, were added to 92.8 mass % of mainly monoclinic zirconia powder. An alumina sol was added so that the amount of addition of alumina is 0.1 mass % to the powder mixture of zirconia and yttria (100 mass %). Then, 150 mass % of water, 0.2 mass % of an anti-foaming agent and 1 mass % of a dispersant were added to the powder mixture of zirconia and yttria (100 mass %). The resulting mixture was pulverized with a ball mill for 10 hours. The average particle size of a slurry obtained by pulverization (ballmilling) was 0.12 µm. The slurry was granulated, using a spray drier, and so formed granules were pre-sintered at 1000° C. for two hours to prepare primary powder.

Next, the primary powder was divided into two groups, and a pigment was added to at least one of the groups. The powder of the group with a low pigment addition ratio is termed a "low addition ratio powder", and that of the group with a high pigment addition ratio is termed a "high addition ratio powder". Table 1 shows the addition ratios of Examples 1 to 3. Table 4 shows the addition ratio of Example 4. The values shown in Tables 1 and 2 are those of addition ratios related to the amount of the powder mixture of zirconia and yttria (100 mass %). In each powder, 0.2 mass % of titania, 200 mass % of water, 0.2 mass % of an anti-foaming agent and 1 mass % of a dispersant were added to the powder mixture of zirconia and yttria (100 mass %). Each resulting mixture was pulverized with a ballmill for 15 hours. The average particle size of the slurry after the pulverization was 0.13 µm. Then, 6 mass % of the binder and 0.5 mass % of a mold release agent were added to the slurry and mixed with a ball mill for 15 minutes. The resulting slurry was granulated by a spray drier to form secondary powders of the low addition ratio powder and the high addition ratio powder.

The low addition ratio powder and the high addition ratio powder were then mixed in ratios shown in Tables 3 to 6 to form first to fourth powders.

A shaped body sample was then prepared. In Examples 1, 3 and 4, 35 grs of the first powder was charged in a metal mold with an inside size of 82 mm by 25 mm and an upper surface of the first powder was swept. 15 grs of the second powder was then charged on the first powder and the metal mold was vibrated by a vibrator. An upper surface of the second powder was swept off to a flat surface. 15 grs of the third powder was then charged on the second powder and the metal mold was vibrated by the vibrator. An upper surface of the third powder was swept off to a flat surface. 35 grs of the fourth powder was then charged on the third powder and the metal mold was vibrated by the vibrator. An upper surface of the fourth powder was swept off to a flat surface. Example 2 was carried out in the same way as in Examples 1, 3 and 4 except that 50 grs of the first powder and 50 grs of the second powder were charged. An upper mold was then set and the powder mixture was subjected to primary press forming at a surface pressure of 200 kg/cm² for 90 seconds using a uniaxial pressing apparatus. The primary press shaped body sample was subjected to CIP shaping at 1500 kg/cm² for five minutes to prepare a shaped body sample.

The shaped body samples were then fired at 1000° C. for two hours to form a pre-sintered body sample. The pre-sintered body samples were then formed to a shape of a dental crown using the CAD/CAM system (Katana system, Kuraray Noritake Dental Inc.). The pre-sintered body sample was then fired at 1500° C. for two hours to form a sintered body sample. The length of the sintered body along the direction of laminating the first to fourth powders was 8 mm.

In the sintered body samples of each of the Examples 1 to 4, an appearance resembling a natural tooth was presented, with color gradation of from pale yellow to yellow-white color from a region corresponding to the first layer towards a region corresponding to the fourth layer of the composition.

TABLE 1

| Examples 1 to 3 | Erbium oxide/ mass % | Iron oxide/ mass % | Praseodymium oxide/ mass % |
|---|---|---|---|
| Low addition ratio powder | 0.1 | 0.005 | 0.005 |
| High addition ratio powder | 2 | 0.1 | 0.1 |

TABLE 2

| Example 4 | Erbium oxide/ mass % | Iron oxide/ mass % | Praseodymium oxide/ mass % |
|---|---|---|---|
| Low addition ratio powder | 0 | 0 | 0 |
| High addition ratio powder | 2 | 0.1 | 0.1 |

TABLE 3

| Example 1 | First powder | Second powder | Third powder | Fourth powder |
|---|---|---|---|---|
| Low addition ratio powder | 0% | 20% | 80% | 100% |
| High addition ratio powder | 100% | 80% | 20% | 0% |

TABLE 4

| Example 2 | First powder | Second powder |
|---|---|---|
| Low addition ratio powder | 0% | 100% |
| High addition ratio powder | 100% | 0% |

TABLE 5

| Example 3 | First powder | Second powder | Third powder | Fourth powder |
|---|---|---|---|---|
| Low addition ratio powder | 0% | 25% | 75% | 100% |
| High addition ratio powder | 100% | 75% | 25% | 0% |

TABLE 6

| Example 4 | First powder | Second powder | Third powder | Fourth powder |
|---|---|---|---|---|
| Low addition ratio powder | 0% | 25% | 75% | 100% |

TABLE 6-continued

| Example 4 | First powder | Second powder | Third powder | Fourth powder |
|---|---|---|---|---|
| High addition ratio powder | 100% | 75% | 25% | 0% |

[Measurement of Flexural Strength]

The flexural strength of the pre-sintered body samples and the sintered body samples, prepared in Example 4, was measured pursuant to JISR1601. As Comparative Examples, the flexural strength was also measured of the pre-sintered body sample and the sintered body sample, in which no vibration was applied to the powders being charged. Comparative Example 1 is for a pre-sintered body sample and a sintered body sample fabricated from a composition in which each layer was not pressed at the time of charging. Comparative Example 2 is for a pre-sintered body sample and a sintered body sample fabricated from a composition in which each layer was pressed at the time of charging. The flexural strength was measured pursuant to JISR1601. The test sample was cut out so that the longitudinal direction was along the laminating direction. The boundary between the second and third layers was positioned at the center of the test sample, as shown in FIG. 1. The boundary extended along the direction of load application, i.e., along a direction of the least [cross-sectional] area, so as to traverse the test sample. The flexural strength was measured with the load point of the three-point bending test aligned with the boundary position. Table 7 shows measured results.

The flexural strength of the pre-sintered body sample of Example 4 was 40 MPa or more, however, those of the Comparative Examples were not larger than 36 MPa. From this it is seen that imparting vibration at the time of laminating of the powders can lead to improved joining strength between the layers at the stage of the pre-sintered body sample. The flexural strength of the sintered body sample of Example 4 was not less than 1200 MPa, however, those of the Comparative Examples 1, 2 were less than 1100 MPa, thus lower by 100 MPa or more than in Example 4. It has turned out that the joining strength between the layers can be elevated for the sintered body sample as well.

The flexural strengths of the pre-sintered body sample as well as the sintered body sample of Example 4 were similar to those of the sintered body sample fabricated without laminating, as taught in Example 9 explained later, and it was found that the laminating did not cause the lowering of the joining strength. It is thus seen that, by imparting vibration at the time of laminating the powders, the interlayer boundary of the laminated sintered body sample as well as the pre-sintered body sample exhibits strength equivalent to that of a local area other than the boundary.

Primarily, it is presumed that the vibration applied to the powders at the time of the laminating produces partial mixing of the powders of upper and lower layers at the interlayer boundary to lead to an increased joining strength between the layers. Secondarily, it is presumed that, since the first to fourth powders are fabricated by mixing of the two sorts of powders, the difference in properties of the powders is only small to lead to an improved affinity in joining.

TABLE 7

| Sample for measurement | Flexural strength of pre-sintered body/MPa | Flexural strength of sintered body/MPa |
|---|---|---|
| Example 4 (with vibration; without pressing) | 41 | 1219 |
| Comparative Example 1 (no vibration, without pressing) | 35 | 1078 |
| Comparative Example 2 (no vibration; with pressing | 30 | 1009 |

[Measurement of Fracture Toughness]

Fracture toughness was measured of the sintered body sample, fabricated in Example 4, in accordance with JISR1607. The position of the boundary in the test sample was the same as in the above mentioned flexural strength testing. The position of the pressing tip was aligned with the boundary between the second and third powders. As a result, the fracture toughness was 4.3 MPa·m$^{1/2}$. This value is similar to that of the fracture toughness of the sintered body sample fabricated without laminating, as taught in Example 9, shown below, thus indicating that deterioration in fracture toughness was not produced by laminating.

[Measurement of Shrinkage Deformation at the Time of Sintering]

A test sample(s), described above and shown in FIG. 3 and FIG. 4, was fabricated from the pre-sintered body sample, fabricated by being pre-sintered at 1000° C. for two hours as in Example 4, and was fired at 1500° C. for two hours to measure the extent of deformation (d/LX100). The extent of the deformation was measured using the above mentioned measurement method. As a Comparative Example, the same test sample(s) was prepared for each of Comparative Examples 1 and 2, as in the bending test, and the extent of deformation after sintering was measured. Table 4 shows test results.

In the Comparative Examples, the extent of the deformation was 0.15 or larger. In Example 4, the extent of the deformation can be 0.05 or less, indicating that the extent of the deformation can be suppressed appreciably as compared to the Comparative Examples. It is thought from this that, by vibrating the composition at the time of layering the powders of different compositions, it is possible to suppress shrinkage deformation at the time of the sintering more satisfactorily.

Comparison between Comparative Examples 1 and 2 indicates that the extent of the deformation is smaller in Comparative Example 1. From this, it is thought that not performing pressing after charging each layer can lead to more effective suppression of shrinkage deformation at the time of the sintering.

Comparison between the two-layered body sample and the four-layered body sample also indicates that the latter is deformed to a lesser extent than the former. From this, it is thought that an increased number of layers can lead to more effective suppression of shrinkage deformation.

TABLE 8

| Samples | Number of layers | Extent of Deformation (=d/L × 100) |
|---|---|---|
| Example 4 (with vibration; without pressing) | 2 | 0.030 |
|  | 4 | 0.025 |
| Comparative Example 1 (without vibration; without pressing) | 2 | 0.285 |
|  | 4 | 0.190 |
| Comparative Example 2 (without vibration; with pressing) | 2 | 0.500 |
|  | 4 | 0.395 |

[Measurement of Chromaticity and Color Difference]

With regard to the first, second, third and fourth powders of Examples 1 to 4, sintered body samples of the respective powders alone were prepared, and chromaticity values of the L*a*b* color chromaticity diagram were measured. For measurement of the chromaticity values, the sintered body sample was worked to a disc of 14 mm in diameter and 1.2 mm in thickness, and both faces of the disc were polished smooth. A device for measurement of the chromaticity values, manufactured by Olympus Corporation under the trade name of CE100-DC/US, was used for measurement. Based on the results of chromaticity measurement, the color differences ΔE*ab1 to ΔE*ab3 between respective neighboring layers were calculated. The color difference ΔE*ab4 between the first and fourth layers was calculated. In addition, (ΔE*ab1+ΔE*ab2+ΔE*ab3−ΔE*ab4) was calculated. Tables 9-12 show the chromaticity. Table 13 shows the color difference.

It is thought that the chromaticity of the sintered body sample of each powder represents chromaticity of the color locally presented by the zirconia sintered body sample.

In the sintered body sample of the first layer of the four-layered lamination body sample, L* was 58 to 73, a* was 0 to 8 and b* was 14 to 27. In the sintered body sample of the second layer, L* was 64 to 73, a* was 0 to 6 and b* was 16 to 22. In the sintered body sample of the third layer, L* was 70 to 78, a* was −2 to 2 and b* was 5 to 17. In the sintered body sample of the fourth layer, L* was 72 to 84, a* was −2 to 1 and b* was 4 to 15

The color difference between the sintered body sample of the first layer and that of the second layer was 7 to 14. The color difference between the sintered body sample of the second layer and that of the third layer was 10 to 18. The color difference between the sintered body sample of the third layer and that of the fourth layer was 4 to 9. The color difference between the sintered body sample of the first layer and that of the fourth layer was 28 to 36. A value obtained by deducting the color difference between the sintered body sample of the first layer and that of the fourth layer from the sum of the color difference between the sintered body sample of the first layer and that of the second layer, the color difference between the sintered body sample of the second layer and that of the third layer and color difference between the sintered body sample of the third layer and that of the fourth layer was not larger than unity (one)

TABLE 9

| Example 1 | L* | a* | b* |
|---|---|---|---|
| Sintered body of fourth powder | 75.70 | −1.45 | 5.68 |
| Sintered body of third powder | 71.75 | −1.15 | 8.35 |

TABLE 9-continued

| Example 1 | L* | a* | b* |
|---|---|---|---|
| Sintered body of second powder | 67.75 | 4.51 | 16.30 |
| Sintered body of first powder | 58.20 | 7.39 | 26.13 |

TABLE 10

| Example 2 | L* | a* | b* |
|---|---|---|---|
| Sintered body of second powder | 75.70 | −1.45 | 5.68 |
| Sintered body of first powder | 58.20 | 7.39 | 26.13 |

TABLE 11

| Example 3 | L* | a* | b* |
|---|---|---|---|
| Sintered body of fourth powder | 76.10 | −1.42 | 5.85 |
| Sintered body of third powder | 71.27 | 0.86 | 11.22 |
| Sintered body of second powder | 63.03 | 5.25 | 21.75 |
| Sintered body of first powder | 58.20 | 7.35 | 26.50 |

TABLE 12

| Example 4 | L* | a* | b* |
|---|---|---|---|
| Sintered body of fourth powder | 83.95 | −1.87 | 4.15 |
| Sintered body of third powder | 77.00 | 0.25 | 9.29 |
| Sintered body of second powder | 64.12 | 4.95 | 20.24 |
| Sintered body of first powder | 58.20 | 7.35 | 26.50 |

TABLE 13

| Examples | 1 | 2 | 3 | 4 |
|---|---|---|---|---|
| Color difference between third and fourth powders ΔE*ab1 | 4.8 | — | 7.6 | 8.9 |
| Color difference between second and third powders ΔE*ab2 | 10.5 | — | 14.1 | 17.5 |
| Color difference between first and second powders ΔE*ab3 | 14.0 | 28.3 | 7.1 | 8.9 |
| Color difference between first and fourth powders ΔE*ab4 | 28.3 | — | 28.7 | 35.3 |
| (ΔE*ab1 + ΔE*ab2 + ΔE*ab3) − ΔE*ab4 | 1.0 | — | 0.04 | 0.07 |

Example 5

[Measurement of Change in b* Value]

Figure 6:
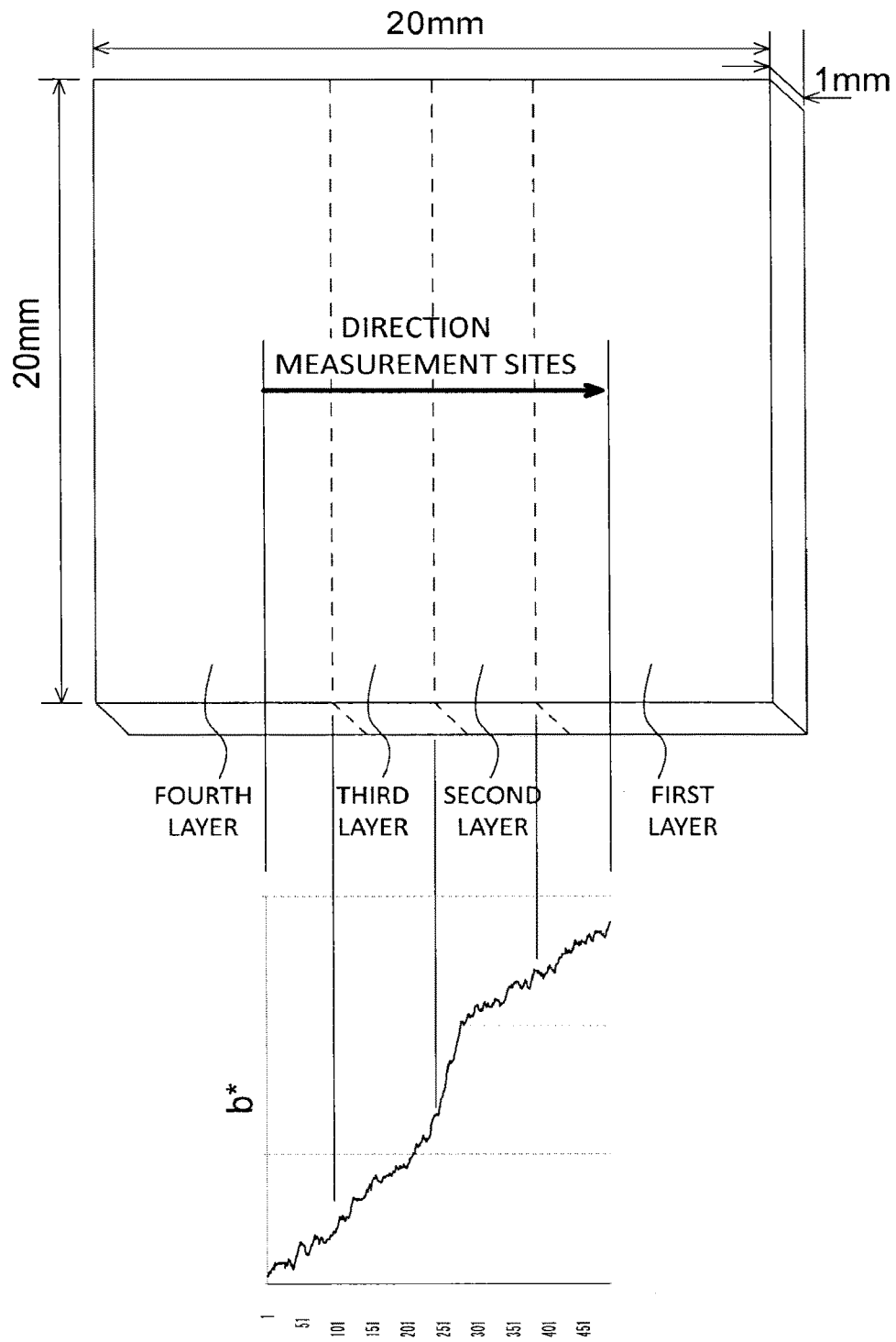
FIG. 6 is a schematic view of a test sample used in Example 5, with a graph showing the results measured.
Figure 7:
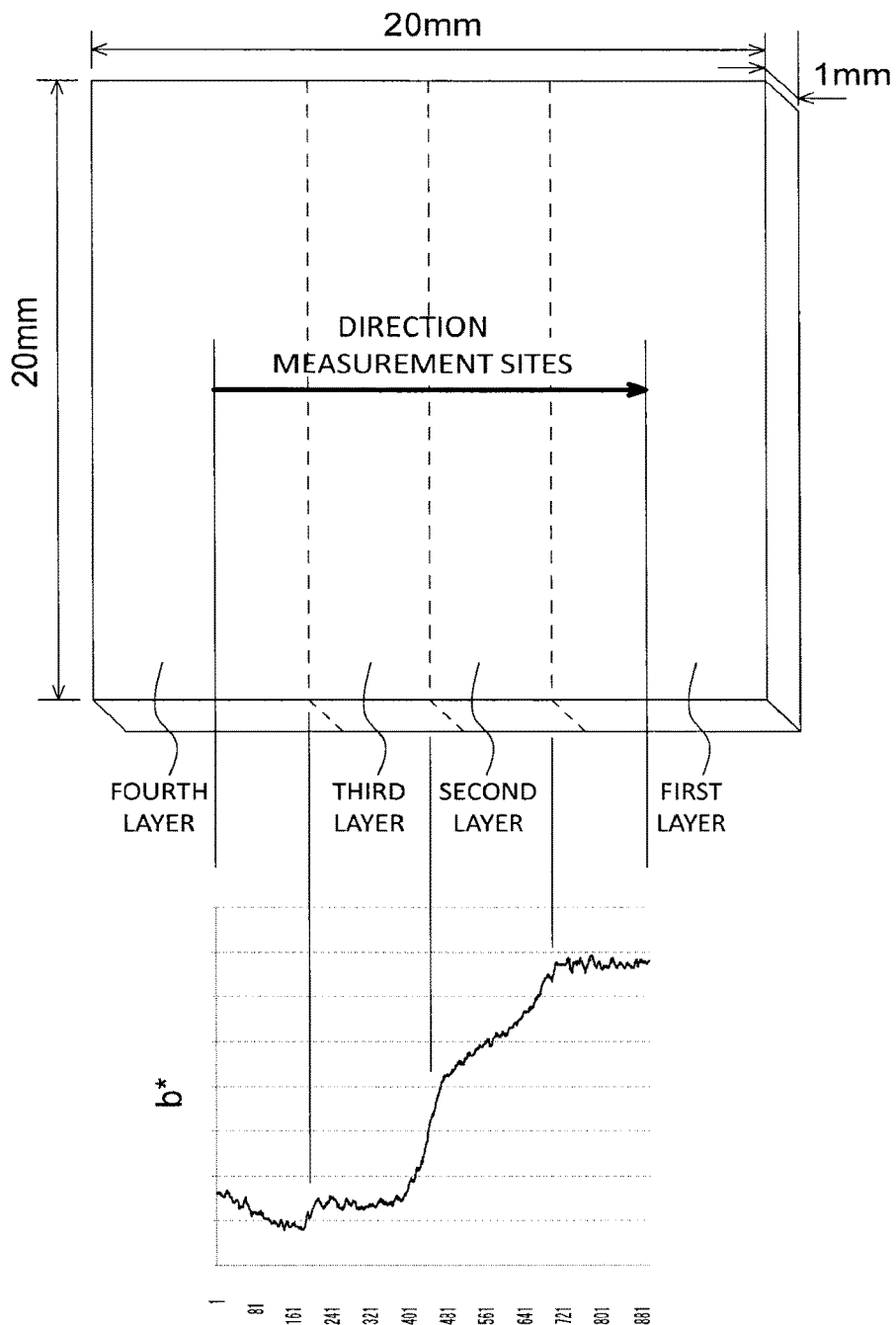
FIG. 7 is a schematic view of a test sample used in Comparative Example 3, with a graph showing the results measured.

Low addition ratio powder and high addition ratio powder were prepared by adding pigments at the rates shown in Table 14 to a powder mixture of zirconia and yttria (100 mass %) and a composition was prepared at the proportions shown in Table 15. From the composition, a sintered body sample was prepared in the same way as in Examples 1 to 4. Change in the value of b* of the L*a*b* color chromaticity diagram was measured along the laminating direction, that is, along the second direction Y in FIG. 2. FIG. 6 depicts a schematic view of the prepared test sample and results of measurement. Specifically, an upper part of FIG. 6 depicts a schematic view of the test sample, also showing the size and the measurement direction, and a lower part of FIG. 6 a graph showing the results of measurement. The as-sintered test sample was fabricated so that the sample has a size of 20 mm by 20 mm by 1 mm after the sintering. The first layer was a local area where the first powders were charged, and the fourth layer was a local area where the fourth powders were charged. The b* value was measured, using a two-dimensional colorimeter RC-300 manufactured and sold by PaPaLaB Co. Ltd., as the test sample was placed at the center of a 29 mm by 22 mm size image, under scanning in a direction perpendicular to the boundaries of the respective layers at an interval of ca. 13 μm. The numerical values entered on the x-axis in the graph of the lower part of FIG. 6 indicate the numbers of measurement points. As a Comparative Example 3, the change in the value of b* was also measured for a sintered body sample obtained without the vibration when the powder of each layer was laminated and with the pressing each time each layer was charged. The composition as well as ratios of the low addition ratio powder and the high addition ratio powder in the Comparative Example 3 was the same as those of Example 5. FIG. 7 depicts a schematic view of the test sample and the results of measurement.

Referring to the graph of FIG. 7, the value of b* shows a flat profile at a center portion of each layer, and, in the interlayer boundary, the value of b* shows step-like acute changes. This is presumably due to the fact that the powders of the respective layers having different pigment compositions have been sintered independently of one another. From this it is seen that there lacks tidy (or smooth) gradation in the appearance of the test sample of Comparative Example 3. On the other hand, referring to the graph of FIG. 6, the value of b* shows a moderately rising tendency even at the center portion of each layer. No step-like changes in the value of b* may be shown at the interlayer boundary such that it is difficult to discern where the boundary is located. In particular, the boundary between the first and second layers and that between the third and fourth layers shows linear transition. From this it is seen that the appearance of the sintered body sample of the present invention presents smooth gradation. This result is thought to be ascribable to the fact that applying the vibration at the time of charging of the first to fourth powders causes the powders to be mixed between the adjacent layers in a region of the boundary between the upper and lower layer, and thus makes it smaller a difference in the pigment ratio between the adjacent layers. By the way, the value of b* is changed more acutely between the second and third layers than at other portions of the graph. This is presumably due to the marked difference in the contents of the pigment(s) between the second and third powders.

TABLE 14

| Example 4 | Erbium oxide/ mass % | Iron oxide/ mass % |
|---|---|---|
| Low addition ratio powder | 0.15 | 0.05 |
| High addition ratio powder | 0.5 | 0.1 |

TABLE 15

| Example 1 | First powder | Second powder | Third powder | Fourth powder |
|---|---|---|---|---|
| Low addition ratio powder | 0% | 20% | 80% | 100% |
| High addition ratio powder | 100% | 80% | 20% | 0% |

Examples 6 to 15

From a composition fabricated by laminating zirconia powders of different pigment compositions, sintered body samples, which are adapted to serve as a dental prosthesis, were fabricated. The chromaticity of the sintered body sample of each powder that forms each layer was measured. The flexural strength, fracture toughness and the peak ratio of the monoclinic crystal following the hydrothermal treatment regarding the sintered body of Example 9 were also measured.

Initially, primary powder was prepared in the same way as in Examples 1 to 4. The primary powder was divided into four sets of powders, that is, first to fourth powders. In Examples 6 to 15, pigments shown in the following Tables 6 to 16 were added to the powders. The numerical values, shown in the Tables, represent values of the addition rates of the pigments to the powder mixture of zirconia and yttria (100 mass %). Secondary powders of the first to fourth powders were prepared in the same way as in Examples 1 to 4 except that the low addition ratio powder and the high addition ratio powder were not fabricated and that different values of the pigments are used.

Then, a shaped body sample was prepared in the same way as in Examples 1 to 4. The shaped body was then fired at 1000° C. for two hours to form a pre-sintered body sample. The pre-sintered body sample was then shaped into a crown shape, using the CAD/CAM system (Katana system, Kuraray Noritake Dental Inc.). The pre-sintered body sample was then fired at 1500° C. for two hours to form a sintered body sample. The length of the sintered body sample of the first to fourth powders along the layering direction was 8 mm.

In each of the sintered body samples of Examples 6 to 16, color gradation changing from pale yellow to yellow-white color was noticed from the local region corresponding to the first layer towards the local region corresponding to the fourth layer of the composition, thus presenting the appearance similar to that of a natural tooth.

TABLE 16

| Example 6 | Erbium oxide/ mass % | Iron oxide/ mass % | Praseodymium oxide/ mass % | Chromium oxide/ mass % |
|---|---|---|---|---|
| Fourth powder | 0 | 0 | 0 | 0 |
| Third powder | 0.02 | 0.04 | 0 | 0.0002 |
| Second powder | 0.08 | 0.16 | 0 | 0.0008 |
| First powder | 0.10 | 0.20 | 0 | 0.0010 |

TABLE 17

| Example 7 | Erbium oxide/ mass % | Iron oxide/ mass % | Praseodymium oxide/ mass % | Chromium oxide/ mass % |
|---|---|---|---|---|
| Fourth powder | 0 | 0 | 0 | 0 |
| Third powder | 0.1 | 0.02 | 0 | 0.0002 |
| Second powder | 0.4 | 0.08 | 0 | 0.0008 |
| First powder | 0.5 | 0.10 | 0 | 0.0010 |

TABLE 18

| Example 8 | Erbium oxide/ mass % | Iron oxide/ mass % | Praseodymium oxide/ mass % | Chromium oxide/ mass % |
|---|---|---|---|---|
| Fourth powder | 0.10 | 0 | 0 | 0 |
| Third powder | 0.15 | 0.026 | 0 | 0.0002 |
| Second powder | 0.30 | 0.104 | 0 | 0.0008 |
| First powder | 0.35 | 0.130 | 0 | 0.0010 |

TABLE 19

| Example 9 | Erbium oxide/ mass % | Iron oxide/ mass % | Praseodymium oxide/ mass % | Chromium oxide/ mass % |
|---|---|---|---|---|
| Fourth powder | 0.15 | 0.05 | 0 | 0 |
| Third powder | 0.22 | 0.06 | 0 | 0 |
| Second powder | 0.43 | 0.09 | 0 | 0 |
| First powder | 0.50 | 0.10 | 0 | 0 |

TABLE 20

| Example 10 | Erbium oxide/ mass % | Iron oxide/ mass % | Praseodymium oxide/ mass % | Chromium oxide/ mass % |
|---|---|---|---|---|
| Fourth powder | 0.15 | 0.050 | 0 | 0 |
| Third powder | 0.19 | 0.066 | 0 | 0 |
| Second powder | 0.31 | 0.114 | 0 | 0 |
| First powder | 0.35 | 0.130 | 0 | 0 |

TABLE 21

| Example 11 | Erbium oxide/ mass % | Iron oxide/ mass % | Praseodymium oxide/ mass % | Chromium oxide/ mass % |
|---|---|---|---|---|
| Fourth powder | 0 | 0 | 0 | 0 |
| Third powder | 0.07 | 0.014 | 0 | 0 |
| Second powder | 0.28 | 0.056 | 0 | 0 |
| First powder | 0.35 | 0.070 | 0 | 0 |

TABLE 22

| Example 12 | Erbium oxide/ mass % | Iron oxide/ mass % | Praseodymium oxide/ mass % | Chromium oxide/ mass % |
|---|---|---|---|---|
| Fourth powder | 0.10 | 0.005 | 0.005 | 0 |
| Third powder | 0.48 | 0.024 | 0.024 | 0 |
| Second powder | 1.62 | 0.081 | 0.081 | 0 |
| First powder | 2.00 | 0.100 | 0.100 | 0 |

TABLE 23

| Example 13 | Erbium oxide/ mass % | Iron oxide/ mass % | Praseodymium oxide/ mass % | Chromium oxide/ mass % |
|---|---|---|---|---|
| Fourth powder | 0.10 | 0.005 | 0 | 0 |
| Third powder | 0.15 | 0.030 | 0.001 | 0 |
| Second powder | 0.30 | 0.105 | 0.004 | 0 |
| First powder | 0.35 | 0.130 | 0.005 | 0 |

TABLE 24

| Example 14 | Erbium oxide/ mass % | Iron oxide/ mass % | Praseodymium oxide/ mass % | Chromium oxide/ mass % |
|---|---|---|---|---|
| Fourth powder | 0 | 0 | 0 | 0 |
| Third powder | 0.02 | 0.001 | 0.001 | 0 |
| Second powder | 0.08 | 0.004 | 0.004 | 0 |
| First powder | 0.10 | 0.005 | 0.005 | 0 |

TABLE 25

| Example 15 | Erbium oxide/ mass % | Iron oxide/ mass % | Praseodymium oxide/ mass % | Chromium oxide/ mass % |
|---|---|---|---|---|
| Fourth powder | 0.5 | 0.025 | 0.025 | 0 |
| Third powder | 0.8 | 0.040 | 0.040 | 0 |
| Second powder | 1.7 | 0.085 | 0.085 | 0 |
| First powder | 2.0 | 0.100 | 0.100 | 0 |

The chromaticity and the color difference of the sintered body samples of the first to fourth powders were measured in the same way as in Examples 1 to 4. Tables 26 to 35 show the values of chromaticity. Tables 36, 37 show the values of the color difference.

It is thought that chromaticity of each powder represents chromaticity of each point of the zirconia sintered body sample fabricated from layered body samples of a plurality of powders. The combination of the four sintered body samples of Example 9 presents bright color on the whole. On the other hand, the combination of the four sintered body samples of Example 10 presents dark color on the whole.

In the sintered body sample of the first layer, $L^*$ was 58 to 76, $a^*$ was −2 to 8 and $b^*$ was 5 to 27. In the sintered body sample of the second layer, $L^*$ was 66 to 81, $a^*$ −2 to 6 and $b^*$ 4 to 21. In the sintered body sample of the third layer, $L^*$ was 69 to 83, $a^*$ −2 to 2 and $b^*$ 3 to 17. In the sintered body sample of the fourth layer, $L^*$ was 71 to 84, $a^*$ −2 to 1 and $b^*$ 2 to 15.

The color difference between the sintered body sample of the first layer and that of the second layer was 3 to 15. The color difference between the sintered body sample of the second layer and that of the third layer was 1 to 11. The color difference between the sintered body sample of the third layer and that of the fourth layer was 1 to 4. The color difference between neighboring layers showed a decreasing tendency from the first layer towards the fourth layer. The color difference between the sintered body sample of the first layer and that of the fourth layer was 8 to 29. A value obtained by deducting the color difference between the sintered body sample of the first layer and that of the fourth layer from the sum of the color difference between the sintered body sample of the first layer and that of the second layer, the color difference between the sintered body sample of the second layer and that of the third layer and the color difference between the sintered body sample of the third layer and the fourth layer was not larger than unity.

TABLE 26

| Example 6 | L* | a* | b* |
|---|---|---|---|
| Fourth powder | 71.97 | 0.60 | 2.10 |
| Third powder | 70.36 | 0.61 | 4.44 |
| Second powder | 68.77 | 0.82 | 11.22 |
| First powder | 64.79 | 0.93 | 19.76 |

TABLE 27

| Example 7 | L* | a* | b* |
|---|---|---|---|
| Fourth powder | 74.33 | −0.75 | 5.24 |
| Third powder | 73.72 | −0.63 | 6.35 |
| Second powder | 73.11 | 1.70 | 9.59 |
| First powder | 71.59 | 2.92 | 13.65 |

TABLE 28

| Example 8 | L* | a* | b* |
|---|---|---|---|
| Fourth powder | 71.97 | 0.60 | 2.10 |
| Third powder | 71.38 | 0.64 | 3.68 |
| Second powder | 70.80 | 1.37 | 8.27 |
| First powder | 69.35 | 1.76 | 14.04 |

TABLE 29

| Example 9 | L* | a* | b* |
|---|---|---|---|
| Fourth powder | 73.79 | −0.90 | 6.64 |
| Third powder | 73.30 | −0.78 | 7.57 |
| Second powder | 72.81 | 1.65 | 10.26 |
| First powder | 71.59 | 2.92 | 13.65 |

TABLE 30

| Example 10 | L* | a* | b* |
|---|---|---|---|
| Fourth powder | 73.79 | −0.90 | 6.64 |
| Third powder | 72.80 | −0.82 | 7.62 |
| Second powder | 71.81 | 0.88 | 10.46 |
| First powder | 69.35 | 1.76 | 14.04 |

TABLE 31

| Example 11 | L* | a* | b* |
|---|---|---|---|
| Fourth powder | 83.97 | −1.89 | 4.17 |
| Third powder | 81.18 | −1.78 | 5.04 |
| Second powder | 78.42 | 0.37 | 7.57 |
| First powder | 71.52 | 1.49 | 10.75 |

TABLE 32

| Example 12 | L* | a* | b* |
|---|---|---|---|
| Fourth powder | 75.77 | −1.41 | 5.70 |
| Third powder | 71.82 | −1.13 | 8.40 |
| Second powder | 67.92 | 4.47 | 16.24 |
| First powder | 58.16 | 7.40 | 26.1 |

TABLE 33

| Example 13 | L* | a* | b* |
|---|---|---|---|
| Fourth powder | 75.77 | −1.41 | 5.70 |
| Third powder | 74.33 | −1.31 | 6.80 |
| Second powder | 72.91 | 0.71 | 10.01 |
| First powder | 69.35 | 1.76 | 14.04 |

TABLE 34

| Example 14 | L* | a* | b* |
|---|---|---|---|
| Fourth powder | 83.97 | −1.89 | 4.17 |
| Third powder | 82.13 | −1.87 | 4.37 |
| Second powder | 80.31 | −1.57 | 4.96 |
| First powder | 75.77 | −1.41 | 5.70 |

TABLE 35

| Example 15 | L* | a* | b* |
|---|---|---|---|
| Fourth powder | 72.49 | 0.97 | 14.5 |
| Third powder | 69.28 | 1.18 | 16.03 |
| Second powder | 66.10 | 5.26 | 20.49 |
| First powder | 58.16 | 7.40 | 26.10 |

TABLE 36

| Examples | 6 | 7 | 8 | 9 | 10 |
|---|---|---|---|---|---|
| Color difference between third and fourth powders ΔE*ab1 | 2.8 | 1.3 | 1.7 | 1.1 | 1.4 |
| Color difference between second and third powders ΔE*ab2 | 7.0 | 4.0 | 4.7 | 3.7 | 3.5 |
| Color difference between first and second powders ΔE*ab3 | 9.4 | 4.5 | 6.0 | 3.8 | 4.4 |
| Color difference between first and fourth powders ΔE*ab4 | 19.1 | 9.6 | 12.3 | 8.3 | 9.0 |
| (ΔE*ab1 + ΔE*ab2 + ΔE*ab3) − ΔE*ab4 | 0.1 | 0.2 | 0.1 | 0.3 | 0.3 |

TABLE 37

| Examples | 11 | 12 | 13 | 14 | 15 |
|---|---|---|---|---|---|
| Color difference between third and fourth powders ΔE*ab1 | 2.9 | 4.8 | 1.8 | 1.9 | 3.6 |
| Color difference between second and third powders ΔE*ab2 | 4.3 | 10.4 | 4.0 | 1.9 | 6.8 |
| Color difference between first and second powders ΔE*ab3 | 7.7 | 14.2 | 5.5 | 4.6 | 10.0 |
| Color difference between first and fourth powders ΔE*ab4 | 14.5 | 28.4 | 11.0 | 8.4 | 19.5 |
| (ΔE*ab1 + ΔE*ab2 + ΔE*ab3) − ΔE*ab4 | 0.4 | 1.0 | 0.3 | 0 | 0.9 |

A zirconia sintered body sample was independently prepared from each of the first to fourth powders of Example 9 and the flexural strength, fracture toughness and the peak ratio of the monoclinic crystal following the hydrothermal treatment were measured. The results of measurement are shown in Table 38. The flexural strength of the zirconia sintered body sample was measured pursuant to JISR1601. The fracture toughness of the zirconia sintered body sample was measured pursuant to JISR1607. The hydrothermal treatment test was conducted pursuant to ISO13356 under a condition of at 180° C., 1 MPa for five hours. After the hydrothermal treatment test, the X-ray diffraction pattern of the zirconia sintered body sample was measured, using CuKα rays, to measure the peak ratio of the monoclinic crystal, that is, the extent of phase transition to the monoclinic crystal caused by the hydrothermal treatment test. In any of the sintered body samples, the flexural strength was not less than 1200 MPa, the fracture toughness was not less than 4 MPa·m$^{1/2}$ and the peak ratio of the monoclinic crystal was not larger than unity. It is thought that, since the zirconia sintered body samples of the other Examples are similar in composition, similar results would be obtained with these Examples. Test results of the flexural strength and the fracture toughness were similar to those obtained with the load applied to the boundary of the laminated body samples.

As for the second powders, the flexural strength of the pre-sintered body sample, prepared by firing at 1000° C. for two hours, was also measured pursuant to JISR1601. The flexural strength of the sintered body sample of the second powder was 41 MPa. This value was similar to that obtained on testing under a load applied to the boundary of the laminated body samples.

TABLE 38

| Samples for measurement | Flexural strength/ MPa | Fracture toughness/ MPa · √m | Peak ratio * of monoclinic crystal |
|---|---|---|---|
| Sintered body of first powders | 1210 | 4.3 | 0.58 |
| Sintered body of second powders | 1216 | 4.3 | 0.59 |
| Sintered body of third powders | 1204 | 4.3 | 0.60 |
| Sintered body of fourth powders | 1202 | 4.3 | 0.59 |

Example 16

In the above Examples, the content of yttria was 4 mol % in terms of the total mols of zirconia and yttria. In Example 16, a sintered body sample with the yttria content of 3 mol % was prepared to measure the chromaticity. Except the yttria content, the sintered body sample used for measurement was the same as that of Example 4 shown in Tables 14 and 15. Table 39 shows measured results. Comparison with the chromaticity shown in Table 12 indicates that, if the yttria content is lowered, L* tends to decrease, while a* and b* tend to increase.

TABLE 39

| Example 16 | L* | a* | b* |
|---|---|---|---|
| Sintered body of fourth powders | 73.20 | −1.35 | 5.72 |
| Sintered body of third powders | 69.78 | 0.42 | 9.84 |
| Sintered body of second powders | 59.52 | 5.75 | 22.20 |
| Sintered body of first powders | 56.10 | 7.52 | 26.32 |

The zirconia sintered body as well as the composition and the pre-sintered body for the zirconia sintered body has been explained in the above exemplary embodiments. It should be noted however that the present invention is not limited to the above described exemplary embodiments and a variety of modifications, changes and improvements may be made of the elements herein disclosed, inclusive of elements of claims, exemplary embodiments and Examples as well as drawings, within the scope of the invention, based on the fundamental technical concept of the present invention. It is also possible to make a diversity of combinations, substitutions and selections of elements herein disclosed, inclusive of elements of claims, exemplary embodiments and Examples as well as drawings, within the scope of the invention.

Further problems, objects and development embodiments of the present invention will become apparent from the entire disclosures inclusive of the claims.

It should be understood that, as regards the range of numerical values, any arbitrary numerical values or sub-ranges contained in the ranges of numerical values set out herein ought to be construed that they are explicitly stated even in the absence of such explicit statements in the present description.

Part or all of the above described exemplary embodiments may also be stated as in supplementary notes shown below, though not restrictively.

[Supplementary Note 1]
A zirconia sintered body, which has
a flexural strength of not less than 1100 MPa measured on a test sample of the zirconia sintered body pursuant to JISR1601;
the test sample being formed by:
preparing a plurality of zirconia powders, each containing zirconia and a stabilizer(s) that suppresses phase transition of zirconia, the plurality of zirconia powders differing in composition;
laminating the plurality of the zirconia powders to form a zirconia lamination composition; and
sintering the zirconia lamination composition to form a zirconia sintered body;
the flexural strength being measured under a condition that a load point of a three-point bending test is positioned at a position of an interlayer boundary of the plurality of zirconia powders, the interlayer boundary traversing the test sample of the sintered body along a direction of load application.

[Supplementary Note 2]
The zirconia sintered body according to supplementary note, wherein;
the flexural strength is not less than 1200 MPa.

[Supplementary Note 3]
The zirconia sintered body according to supplementary note, wherein;
when a zirconia pre-sintered body is prepared by pre-sintering the zirconia composition at 800° C. to 1200° C., a flexural strength of a test sample of the pre-sintered body, measured pursuant to JISR1601, is not less than 90% of a flexural strength of the zirconia pre-sintered body obtained by pre-sintering one composition of the plurality of zirconia powders alone at the same temperature as a pre-sintering temperature of the test sample,
the flexural strength being measured under the condition that a load point of the three-point bending test is positioned at the position of the interlayer boundary of the plurality of zirconia powders, the interlayer boundary traversing the test sample of the sintered body along the direction of load application.

[Supplementary Note 4]
The zirconia sintered body according to supplementary note, wherein, the plurality of zirconia powders contain a pigment(s) in different ratios, respectively.

[Supplementary Note 5]
The zirconia sintered body according to supplementary note, wherein, the flexural strength, as measured pursuant to JISR1601, of each sintered body, obtained by sintering one composition of the plurality of zirconia powders alone at 1500° C., is not less than 1100 MPa.

[Supplementary Note 6]
A zirconia pre-sintered body, which has
a flexural strength of a test sample of the zirconia pre-sintered body, measured pursuant to JISR1601, which is not less than 90% of the flexural strength of a comparative zirconia pre-sintered body;
the test sample being formed by:
preparing a plurality of zirconia powders, each containing zirconia and a stabilizer that suppresses phase transition of zirconia, the plurality of zirconia powders differing in composition;
laminating the plurality of zirconia powders to form a zirconia lamination composition; and
pre-sintering the zirconia lamination composition at 800° C. to 1200° C. to form a zirconia pre-sintered body;
the comparative zirconia pre-sintered body being formed by pre-sintering one composition of the plurality of zirconia powders alone at the same temperature as a pre-sintering temperature of the test sample;
the flexural strength being measured under a condition that a load point of a three-point bending test is positioned at a position of an interlayer boundary of the zirconia powders, the interlayer boundary traversing the test sample of the pre-sintered body along a direction of load application.

[Supplementary Note 7]
The zirconia sintered body according to supplementary note, wherein, the plurality of zirconia powders contain a pigment(s) in different ratios, respectively.

[Supplementary Note 8]
A zirconia pre-sintered body, wherein,
when a test sample is placed on a ground with one of two bottom surfaces that has been deformed to a concave shape directed downwards; (a maximum gap between a deformed concave bottom surface and a ground surface)/(distance between portions of the test sample contacting the ground surface along a widthwise direction)×100 is 0.15 or less,
the test sample being formed by:
preparing a plurality of zirconia powders, each containing zirconia and a stabilizer(s) that suppresses phase transition of zirconia, the plurality of zirconia powders differing in composition;
laminating the plurality of zirconia powders to form a zirconia composition;
firing the zirconia composition at 800° C. to 1200° C. to form a zirconia pre-sintered body; the pre-sintered body being shaped to a form of a rectangular parallelepiped 50 mm in width[length], 10 mm in height and 5 mm in depth[thickness] as the test sample, and two surfaces of the test sample of 50 mm in width and 5 mm in depth are taken to be the bottom surfaces; boundary surfaces formed by laminating of the plurality of zirconia powders extending in the same direction as the bottom surfaces; and
sintering the pre-sintered body at 800° C. to 1200° C. for two hours.

[Supplementary Note 9]
The zirconia pre-sintered body according to the supplementary note, wherein (the maximum gap between the deformed concave bottom surface and the ground surface)/(distance between the portions of the test sample contacting the ground surface along the widthwise direction)×100 is 0.1 or less.

[Supplementary Note 10]
The zirconia pre-sintered body according to the supplementary note, wherein the plurality of zirconia powders contain a pigment(s) in respective different ratios.

[Supplementary Note 11]

The zirconia sintered body according to the supplementary note, wherein,
the zirconia sintered body is prepared by a method comprising: sintering the zirconia pre-sintered body at 1400° C. to 1600° C.

INDUSTRIAL APPLICABILITY

The zirconia sintered body according to the present invention may be put to a variety of uses, including dental materials, such as prostheses, connection parts for optical fibers, such as ferrules and sleeves, a variety of tools, such as crushing balls and grinding tools, a variety of components, such as screws, bolts and nuts, a variety of sensors, electronic parts, and ornaments, such as watch bands. In using the zirconia sintered body for a dental material, it may be used as, for example, coping, a framework, a crown, a crown bridge, an abutment, an implant, an implant screw, an implant fixture, an implant bridge, an implant bar, a bracket, a dental plate, inlay, unlay, onlay, a wire for correction or a laminate veneer.

REFERENCE SIGNS LIST 10 zirconia sintered body
20, 22 pre-sintered body
20a, 22a bottom surface
21a, 22a first and second surfaces
23a to 23d first to fourth layers
30 ground surface
A to D first to fourth points
P one end
Q opposite end
X first direction
Y second direction

What is claimed is:

1. A method for preparing a zirconia composition, comprising:
preparing a plurality of powders each comprising zirconia, a stabilizer capable of suppressing phase transition of zirconia, and a pigment, such that the powders have different content ratios of the pigment; and
charging the powders into a mold to form a laminate of layers of the powders in the mold,
wherein during the charging, the mold is vibrated after at least two layers of the powders are formed in the mold such that the powders at an interlayer boundary of two contacting layers are partially mixed while maintaining shapes of the powders and that color gradation is imparted at the interlayer boundary.

2. The method according to claim 1, wherein during the charging, the mold is vibrated after each layer of the plurality of powders is formed in the mold such that color gradation is imparted at each interlayer boundary of two contacting layers.

3. The method according to claim 1, wherein during the charging, after one powder is charged into the mold, an upper surface of a layer of the powder is flattened.

4. The method according to claim 1, wherein during the charging, the powders are charged such that the layers in the laminate have pigment contents varied in order.

5. A method for preparing a zirconia pre-sintered body, comprising:
preparing a zirconia composition according to the method of claim 1; and
firing the zirconia composition at 800° C. to 1200° C.

6. A method for preparing a zirconia sintered body, comprising:
preparing a zirconia composition according to the method of claim 1; and
firing the zirconia composition at 1400° C. to 1600° C.

7. A method for preparing a zirconia sintered body, comprising:
preparing a zirconia pre-sintered body according to the method of claim 5; and
firing the pre-sintered body at 1400° C. to 1600° C.

8. The method according to claim 1, wherein, in the preparing, a first powder having a first content ratio of the pigment and a second powder having a second content ratio of the pigment higher than the first content ratio are mixed at varying mixing ratios to prepare the plurality of powders.

9. The method according to claim 1, wherein the plurality of powders are charged into the mold such that the layers in the laminate have gradually decreasing or increasing content ratio of the pigment.

10. The method according to claim 1, wherein the mold is vibrated by applying a mechanical vibration to the mold, manually vibrating or swinging the mold, striking the mold with a hammer, or a combination thereof.

11. The method according to claim 1, wherein the zirconia composition includes silicon oxide ($SiO_2$) in an amount of not greater than 0.1 mass % relative to a total mass of the zirconia and the stabilizer.

12. The method according to claim 1, wherein, in the charging, the laminate of layers is formed such that a color of a zirconia sintered body prepared by firing the zirconia composition continuously changes in a first direction to increase the L* value and decrease the a* and b* values in the L*a*b* color chromaticity diagram, the first direction being a direction of the laminate.

13. The method according to claim 12, wherein, in the charging, the laminate of layers is formed such that the color of the zirconia sintered body does not change in a second direction perpendicular to the first direction.

14. The method according to claim 12, wherein, on a straight line in the first direction extending from one end to an opposite end of the zirconia sintered body,
a first point in a domain from the one end to a point of 25% of a total length from the one end to the opposite end has a chromaticity (L1, a1, b1) in the L*a*b* color chromaticity diagram where L1 is from 58.0 to 76.0, a1 is from −1.6 to 7.6, and b1 is from 5.5 to 26.7,
a second point in a domain from the opposite end to a point of 25% of the total length has a chromaticity (L2, a2, b2) in the L*a*b* color chromaticity diagram where L2 is from 71.8 to 84.2, a2 is from −2.1 to 1.8, and b2 is from 1.9 to 16.0, $L1 < L2$, $a1 > a2$, and $b1 > b2$.

15. The method according to claim 1, wherein the at least two layers of the powders are not pressed before the mold is vibrated.

* * * * *